United States Patent
Lin et al.

(10) Patent No.: US 11,319,602 B2
(45) Date of Patent: May 3, 2022

(54) PROBE COMBINATION FOR DETECTION OF CANCER

(71) Applicant: TCM BIOTECH INTERNATIONL CORP., New Taipei (TW)

(72) Inventors: You-Yu Lin, Taipei (TW); Ya-Chun Wang, New Taipei (TW); Sheng-Tai Tzeng, New Taipei (TW)

(73) Assignee: TCM BIOTECH INTERNATIONL CORP., New Taipei (TW)

( * ) Notice: Subject to any disclaimer, the term of this patent is extended or adjusted under 35 U.S.C. 154(b) by 222 days.

(21) Appl. No.: 15/885,717

(22) Filed: Jan. 31, 2018

(65) Prior Publication Data

US 2018/0223380 A1    Aug. 9, 2018

Related U.S. Application Data

(60) Provisional application No. 62/456,087, filed on Feb. 7, 2017.

(51) Int. Cl.
    C12Q 1/68        (2018.01)
    C07H 21/04       (2006.01)
    C12Q 1/70        (2006.01)
    C12Q 1/6886      (2018.01)

(52) U.S. Cl.
    CPC .......... *C12Q 1/706* (2013.01); *C12Q 1/6886* (2013.01)

(58) Field of Classification Search
    None
    See application file for complete search history.

(56) References Cited

U.S. PATENT DOCUMENTS

2012/0309643 A1* 12/2012 Wong ................... C12Q 1/6813
                                                  506/9
2018/0237863 A1*  8/2018 Namsaraev ............ C12Q 1/686

FOREIGN PATENT DOCUMENTS

| CN | 102277448 A    | 12/2011 |
| CN | 103797130 B    | 7/2016  |
| JP | 2009-504153 A  | 2/2009  |
| KR | 10-1162088 B1  | 7/2012  |
| TW | 201321519 A1   | 6/2013  |

(Continued)

OTHER PUBLICATIONS

Lin et al. (BMC Bioinformatics, vol. 18, No. 223, 2017). (Year: 2017).*

(Continued)

*Primary Examiner* — Jeanine A Goldberg
(74) *Attorney, Agent, or Firm* — ScienBiziP, P.C.

(57) ABSTRACT

A probe combination for detecting cancer includes one or more sets of partial hepatitis B virus (HBV) targeting probes. When sequences of each of the sets of partial HBV targeting probes are aligned, an overall sequence of the aligned set of probes matches a reference sequence of a genome of a HBV genotype or a direct repeat (DR) region on the genome. In the aligned set of probes, each of the probes overlap with one or two adjacent probes by a portion of a length of the probe. The probe combination may further includes one or more sets of hotspot gene targeting probes targeting cancer hotspot genes such as CTNNB1, TERT, and TP53 genes, one or more sets of exogenous gene targeting probes targeting portions of a lambda phage genome, and endogenous gene targeting probes targeting endogenous genes such as GAPDH and GdX genes.

28 Claims, 8 Drawing Sheets

Specification includes a Sequence Listing.

(56) References Cited

FOREIGN PATENT DOCUMENTS

TW          201321566 A1     6/2013
WO       2016/205572 A1    12/2016

OTHER PUBLICATIONS

Li et al. (Genomics, vol. 102, pp. 338-344, 2013). (Year: 2013).*
*Drosophila* Tiling 2.0R array design and library files (Sep. 26, 2007, Revision Version: 1.0). (Year: 2007).*
NEB catalog (1998/1999), pp. 121,284. (Year: 1998).*
Zhaoshi Jiang, et al., "The effects of hepatitis B virus integration into the genomes of hepatocellular carcinoma patients", Genome Res. (2012) 22, 593-601.
Wing-Kin Sung, et al., "Genome-wide survey of recurrent HBV integration in hepatocellular carcinoma", Nature Genetics (2012) 44, 765-769.
Weiyang Li, et al., "HIVID: An efficient method to detect HBV integration using low coverage sequencing", Genomics (2013) 102:4, 338-344.
Ling-Hao Zhao, et al., "Genomic and oncogenic preference of HBV integration in hepatocellular carcinoma", Nature Communications (2016) 7:12992.
You-Yu Lin, et al., "De novo assembly of highly polymorphic metagenomic data using in situ generated reference sequences and a novel BLAST-based assembly pipeline" BMC Bioinformatics 2017; 18:223.
Li Weiyang et al: "HIVID: An efficient method to detect HBV integration using low coverage sequencing", Genomics, vol. 102, No. 4, Jul. 15, 2013 (Jul. 15, 2013), pp. 338-344, XP028751656, ISSN: 0888-7543, DOI: 10.1016/J.YGENO.2013.07.002 abstract; p. 339, paragraph 1; figures 1-6.
Ling-Hao Zhao et al: "Genomic and oncogenic preference of HBV integration in hepatocellular carcinoma", Nature Communications, vol. 7, No. 1, Oct. 5, 2016 (Oct. 5, 2016), XP055657673, DOI: 10.1038/ncomms12992 abstract, "HBV capture experiment" on p. 8.
Lee SE et al., "Frequent somatic TERT promoter mutations and CTNNB1 mutations in hepatocellular carcinoma", Oncotarget. Oct. 25, 2016; 7(43): 69267-69275. Abstract; p. 69273 left column first paragraph last lines 1-5.
Laskus T et al., "Detection and Sequence Analysis of Hepatitis B Virus Integration in Peripheral Blood Mononuclear Cells", J Virol. Feb. 1999; 73(2): 1235-8. Abstract; p. 1236 left column first paragraph.
Lin H et al., "An oligonucleotide probe for the detection of hepatitis B virus DNA in serum", J Virol Methods. Feb. 1987; 15(2): 139-49. Abstract; p. 147 last paragraph.

* cited by examiner

2X Tiling Density

4X Tiling Density

| Female HBV HCC | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| JunctionType | 6 | 10 | 8 | 6 | 7 | 13 | 9 | 2 | 1 | 9 | 2 | 4 | 9 | 2 | 4 | 2 | 5 | 2 | 2 | 4 | 6 | 7 | 2 | 4 | 10 |
| TERT integration | 1 | 1 | 1 | 1 | 1 | 0 | 0 | 0 | 0 | 0 | 0 | 0 | 0 | 0 | 0 | 0 | 0 | 0 | 0 | 0 | 0 | 0 | 0 | 0 | 0 |
| MLL4 integration | 0 | 0 | 0 | 0 | 0 | 1 | 1 | 1 | 1 | 1 | 0 | 0 | 0 | 0 | 0 | 0 | 0 | 0 | 0 | 0 | 0 | 0 | 0 | 0 | 0 |
| TERT mutation | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 |
| CTNNB1 mutations | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| Male HBV HCC | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| JunctionType | 5 | 2 | 2 | 11 | 5 | 6 | 5 | 4 | 12 | 8 | 6 | 4 | 4 | 73 | 4 | 6 | 4 | 7 | 0 | 2 | 6 | 3 | 4 | 8 | 7 |
| TERT integration | 1 | 1 | 1 | 1 | 1 | 1 | 1 | 1 | 1 | 1 | 1 | 1 | 0 | 0 | 0 | 0 | 0 | 0 | 0 | 0 | 0 | 0 | 0 | 0 | 0 |
| MLL4 integration | 0 | 0 | 0 | 0 | 0 | 0 | 0 | 0 | 0 | 0 | 0 | 0 | 1 | 1 | 1 | 1 | 1 | 1 | 1 | 0 | 0 | 0 | 0 | 0 | 0 |
| TERT mutation | 0 | 0 | 0 | 0 | 0 | 0 | 0 | 0 | 0 | 0 | 0 | 0 | 0 | 0 | 0 | 0 | 0 | 0 | 0 | 1 | 1 | 1 | 1 | 0 | 0 |
| CTNNB1 mutations | 1 | 1 | 1 | 1 | 1 | 0 | 0 | 0 | 0 | 0 | 0 | 0 | 0 | 0 | 0 | 0 | 0 | 0 | 0 | 0 | 0 | 0 | 0 | 1 | 0 |

FIG. 7

SEQUENCE LISTING

<160> NUMBER OF SEQ ID NOS: 56

<210> SEQ ID NO 1
<211> LENGTH: 3191
<212> TYPE: DNA
<213> ORGANISM: Hepatitis B virus

```
<400> SEQUENCE: 1
ctccaccact ttccaccaaa ctcttcaaga tcccagagtc agggccctgt actttcctgc      60
tggtggctcc agttcaggaa cagtgagccc tgctcagaat actgtctctg ccatatcgtc     120
aatcttatcg aagactgggg accctgtacc gaacatggag aacatcgcat caggactcct     180 aggaccctg ctcgtgttac aggcggggtt tttcttgttg acaaaatcc tcacaatacc       240 acagagtcta gactcgtggt ggacttctct caattttcta gggggaacac ccgtgtgtct     300
tggccaaaat tcgcagtccc aaatctccag tcactcacca acctgttgtc ctccaatttg     360
tcctggttat cgctggatgt gtctgcggcg ttttatcatc ttcctctgca tcctgctgct     420
atgcctcatc ttcttgttgg ttcttctgga ctatcaaggt atgttgcccg tttgtcctct     480
aattccagga tcatcaacaa ccagcaccgg accatgcaaa acctgcacaa ctcctgctca     540
aggaacctct atgtttccct catgttgctg tacaaaacct acggacggaa actgcacctg     600
tattcccatc ccatcatctt gggctttcgc aaaataccta tgggagtggg cctcagtccg     660
tttctcttgg ctcagtttac tagtgccatt tgttcagtgg ttcgtagggc tttcccccac     720
tgtctggctt tcagttatat ggatgatgtg gtattggggg ccaagtctgt acaacatctt     780
gagtcccttt atgccgctgt taccaatttt cttttgtctt ggggtataca tttaaaccct     840
cacaaaacaa aaagatgggg atattcccct aacttcatgg gatatgtaat tgggagttgg     900
ggcacattgc cacaggaaca tattgtacaa aaaatcaaaa tgtgttttag gaaacttcct     960
gtaaacaggc ctattgattg gaaagtatgt caacgaattg tgggtctttt ggggtttgcc    1020
gcccctttca cgcaatgtgg atatcctgct ttaatgcctt tatatgcatg tatacaagca    1080
aaacaggctt ttacttttctc gccaacttac aaggcctttc taagtaaaca gtatctgaac    1140
ctttaccccg ttgctcggca acggcctggt ctgtgccaag tgtttgctga cgcaaccccc    1200
actggttggg gcttggccat aggccatcag cgcatgcgtg gaacctttgt gtctcctctg    1260
ccgatccata ctgcggaact cctagccgct tgttttgctc gcagcaggtc tggagcaaaa    1320
ctcatcggga ctgacaattc tgtcgtgctc tcccgcaagt atacatcatt ccatggctg     1380 ctaggctgtg ctgccaactg gatcctgcgc gggacgtcct tgtttacgt cccgtcggcg     1440 ctgaatcccg cggacgaccc ctcccggggc cgcttggggc tctaccgccc gcttctccgc    1500
ctgttgtacc gaccgaccac ggggcgcacc tctctttacg cggactcccc gtctgtgcct    1560
tctcatctgc cggaccgtgt gcacttcgct tcacctctgc acgtcgcatg gagaccaccg    1620
tgaacgccca ccggaacctg cccaaggtct tgcataagag gactcttgga ctttcagcaa    1680
tgtcaacgac cgaccttgag gcatacttca aagactgtgt gtttactgag tgggaggagt    1740 tggggggagga gattaggtta aaggtctttg tactaggagg ctgtaggcat aaattggtgt    1800
gttcaccagc accatgcaac ttttcacct ctgcctaatc atctcatgtt catgtcctac     1860
tgttcaagcc tccaagctgt gccttgggtg gctttgggc atggacattg acccgtataa    1920
agaatttgga gcttctgtgg agttactctc tttttgcct tctgacttct ttccttctat    1980
tcgagatctc ctcgacaccg cctctgctct gtatcgggag gccttagagt ctccggaaca    2040
ttgttcacct caccatacgg cactcaggca agctattctg tgttggggtg agttaatgaa    2100
tctagccacc tgggtgggaa gtaatttgga agatccagca tccagggaat tagtagtcag    2160
ctatgtcaac gttaatatgg gcctaaaaat cagacaacta ttgtggttc acatttcctg    2220 tcttactttt ggaagagaaa ctgttcttga atatttggtg tcttttggag tgtggattcg    2280
cactcctcct gcatatagac caccaaatgc ccctatctta tcaacacttc cggaaactac    2340
```

```
tgttgttaga cgaagaggca ggtcccctag aagaagaact ccctcgcctc gcagacgaag    2400
gtctcaatcg ccgcgtcgca gaagatctca atctcgggaa tctcaatgtt agtattcctt    2460
ggacacataa ggtgggaaac tttacggggc tttattcttc tacggtacct tgctttaatc    2520
ctaaatggca aactccttct tttcctgaca ttcatttgca ggaggacatt gttgatagat    2580
gtaagcaatt tgtggggccc cttacagtaa atgaaaacag gagactaaaa ttaattatgc    2640
ctgctaggtt ttatcccaat gttactaaat atttgccctt agataaaggg atcaaacctt    2700
attatccaga gcatgtagtt aatcattact ccagacgag  acattattta cacactcttt    2760
ggaaggcggg tatcttatat aaagagagt  ccacacgtag cgcctcattt tgcgggtcac    2820
catattcttg ggaacaagat ctacagcatg ggaggttggt cttccaaacc tcgaaaaggc    2880
atggggacaa atctttctgt ccccaatccc ctgggattct tccccgatca tcagttggac    2940
cctgcattca aagccaactc agaaaatcca gattgggacc tcaacccgca caaggacaac    3000
tggccggacg ccaacaaggt gggagtggga gcattcgggc cagggttcac ccctccccat    3060
gggggactgt tggggtggag ccctcaggct cagggcatac tcacaactgt gccagcagct    3120
cctcctcctg cctccaccaa tcggcagtca ggaaggcagc ctactccctt atctccacct    3180
ctaagggaca c                                                         3191

<210> SEQ ID NO 2
<211> LENGTH: 3191
<212> TYPE: DNA
<213> ORGANISM: Hepatitis B virus

<400> SEQUENCE: 2
ctccacaaca ttccaccaag ctctgctaga tcccagagtg aggggcctat actttcctgc      60
tggtggctcc agttccggaa cagtaaaccc tgttccgact actgcctcac ccatatcgtc     120
aatcttctcg aggactgggg accctgcacc gaacatggag aacacaacat caggattcct     180
aggacccctg ctcgtgttac aggcggggtt tttcttgttg acaagaatcc tcacaatacc     240
acagagtcta gactcgtggt ggacttctct caattttcta gggggagcac ccacgtgtcc     300
tggccaaaat tcgcagtccc caacctccaa tcactcacca acctcttgtc ctccaatttg     360
tcctggctat cgctggatgt gtctgcggcg ttttatcata ttcctcttca tcctgctgct     420
atgcctcatc ttcttgttgg ttcttctgga ctaccaaggt atgttgcccg tttgtcctct     480
acttccagga acatcaacta ccagcacggg accatgcaag acctgcacga ttcctgctca     540
aggaacctct atgtttccct cttgttgctg tacaaaacct tcggacggaa actgcacttg     600
tattcccatc ccatcatcct gggctttcgc aagattccta tgggagtggg cctcagtccg     660
tttctcctgg ctcagtttac tagtgccatt tgttcagtgg ttcgtagggc tttcccccac     720
tgtttggctt tcagttatat ggatgatgtg gtattggggg ccaagtctgt acaacatctt     780
gagtcccttt taccttctat taccaatttt cttttgtctt gggtataca  tttgaaccct     840 aataaaacca aacgttgggg ctactccctt aacttcatgg gatatgtaat tggaagttgg     900
ggtactttac cacaggaaca tattgtacta aaaatcaagc aatgttttcg aaaactgcct     960
gtaaatagac ctattgattg gaaagtatgt caaagaattg tgggtctttt gggctttgct    1020
gcccctttta cacaatgtgg ctatcctgcc ttaatgcctt tatatgcatg tatacaatct    1080
aagcaggctt tcactttctc gccaacttac aaggcctttc tgtgtaaaca atatctgaac    1140
ctttaccccg ttgcccggca acggtcaggt ctctgccaag tgtttgctga cgcaaccccc    1200
```

```
actgatggg gcttggccat aggccatcgg cgcatgcgtg gaacctttgt ggctcctctg    1260
ccgatccata ctgcggaact cctagcagct tgttttgctc gcagccggtc tggagcgaaa    1320
cttatcggca ccgacaactc tgttgtcctc tctcggaaat acacctcctt ccatggctg     1380 ctagggtgtg ctgccaactg gatcctgcgc gggacgtcct ttgtctacgt cccgtcggcg    1440
ctgaatcccg cggacgaccc gtctcggggc cgtttgggac tctaccgtcc ccttcttcat    1500
ctgccgttcc ggccgaccac ggggcgcacc tctctttacg cggtctcccc gtctgtgcct    1560
tctcatctgc cggaccgtgt gcacttcgct tcacctctgc acgtcgcatg gagaccaccg    1620
tgaacgccca ccaggtcttg cccaaggtct tacataagag gactcttgga ctctcagcaa    1680
tgtcaacgac cgaccttgag gcatacttca aagactgttt gtttaaagac tgggaggagt    1740
tgggggagga gattaggtta atgatctttg tactaggagg ctgtaggcat aaattggtct    1800
gttcaccagc accatgcaac ttttcacct ctgcctaatc atctcatgtt catgtcctac     1860
tgttcaagcc tccaagctgt gccttgggtg gctttgggc atggacattg acccgtataa     1920
agaatttgga gcttctgtgg agttactctc ttttttgcct tctgacttct ttccttctat    1980
tcgagatctc ctcgacaccg cctctgctct gtatcgggag gccttagagt ctccggaaca    2040
ttgttcacct caccatacag cactcaggca agctattctg tgttggggtg agttgatgaa    2100
tctggccacc tgggtgggaa gtaatttgga agacccagca tccagggaat tagtagtcag    2160
ctatgtcaat gttaatatgg gcctaaaaat cagacaacta ttgtggtttc acatttcctg    2220
tcttactttt ggaagagaaa ctgttcttga gtatttggtg tcttttggag tgtggattcg    2280
cactcctccc gcttacagac caccaaatgc ccctatctta tcaacacttc cggaaactac    2340
tgttgttaga cgacgaggca ggtcccctag aagaagaact ccctcgcctc gcagacgaag    2400
gtctcaatcg ccgcgtcgca gaagatctca atctcgggaa tctcaatgtt agtatccctt    2460
ggactcataa ggtgggaaac tttactgggc tttattcttc tactgtacct gtctttaatc    2520
ctgagtggca aactccctcc tttcctcaca ttcatttaca ggaggacatt attaatagat    2580
gtcaacaata tgtgggccct cttacagtta atgaaaaaag gagattaaaa ttaattatgc    2640
ctgctaggtt ctatcctaac cttaccaaat atttgccctt ggataaaggc attaaacctt    2700
attatcctga acatgcagtt aatcattact tcaaaactag gcattattta catactctgt    2760
ggaaggctgg cattctatat aagagagaaa ctacacgcag cgcctcattt tgtgggtcac    2820
catattcttg gaacaagag ctacagcatg ggaggttggt cttccaaacc tcgacaaggc     2880
atggggacga atctttctgt tcccaatcct ctgggattct ttcccgatca ccagttggac    2940
cctgcgttcg gagccaactc aaacaatcca gattgggact caaccccaa caaggatcac     3000 tggccagagg caaatcaggt aggagcggga gcattcgggc cagggttcac ccaccacac     3060 ggcggtcttt tggggtggag ccctcaggct cagggcatat tgacaacagt gccagcagca    3120
cctcctcctg cctccaccaa tcggcagtca ggaagacagc ctactcccat ctctccacct    3180
ctaagagaaa g                                                        3191
```

<210> SEQ ID NO 3
<211> LENGTH: 960
<212> TYPE: DNA
<213> ORGANISM: Hepatitis B virus

<400> SEQUENCE: 3

```
cgcatgcgtg gaaccttttgt ggctcctctg ccgatccata ctgcggaact cctagccgct    60
tgttttgctc gcagccggtc tggagcaaag ctcatcggaa ctgacaattc tgtcgtcctc    120
```

```
tcgcggaaat atacatcgtt ccatggctg ctaggctgtg ctgccaactg gatccttcgc    180
ggaacgtcct ttgtctacgt cccgtcggcg ctgaatcccg cggacgaccc ctctcggggc    240
cgcttgggac tctctcgtcc ccttctccgt ctgccgttcc agccgaccac ggggcgcacc    300
tctctttacg cggtctcccc gtctgtgcct tctcatctgc cggtccgtgt gcacttcgct    360
tcacctctgc acgttgcatg gagaccaccg tgaacgccca tcagatcctg cccaaggtct    420
tacataagag gactcttgga ctcccagcaa tgtcaacgac cgaccttgag gcctacttca    480
aagactgtgt gtttaaggac tgggaggagc tgggggagga gattaggtta aaggtctttg    540
tattaggagg ctgtaggcat aaattggtct gcgcaccagc accatgcaac ttttcacct     600 ctgcctaatc atctcttgta catgtcccac tgttcaagcc tccaagctgt gccttgggtg    660
gctttggggc atggacattg acccttataa agaatttgga gctactgtgg agttactctc    720 gttttttgcct tctgacttct ttccttccgt cagagatctc ctagacaccg cctcagctct    780
gtatcgagaa gccttagagt ctcctgagca ttgctcacct caccatactg cactcaggca    840
agccattctc tgctgggggg aattgatgac tctagctacc tgggtgggta ataatttgga    900
agatccagca tccagggatc tagtagtcaa ttatgttaat actaacatgg gtttaaagat    960
```

<210> SEQ ID NO 4
<211> LENGTH: 960
<212> TYPE: DNA
<213> ORGANISM: Hepatitis B virus

<400> SEQUENCE: 4

```
cgcatgcgtg gaacctttgt ggctcctctg ccgatccata ctgcggaact cctagccgct     60
tgttttgctc gcagccggtc tggagcaaag ctcatcggaa ctgacaattc tgtcgtcctc    120
tcgcggaaat atacatcgtt ccatggctg ctaggctgta ctgccaactg gatccttcgc    180
gggacgtcct ttgtttacgt cccgtcggcg ctgaatcccg cggacgaccc ctctcggggc    240
cgcttgggac tctctcgtcc ccttctccgt ctgccgttcc agccgaccac ggggcgcacc    300
tctctttacg cggtctcccc gtctgtgcct tctcatctgc cggtccgtgt gcacttcgct    360
tcacctctgc acgttgcatg gagaccaccg tgaacgccca tcagatcctg cccaaggtct    420
tacataagag gactcttgga ctcccagcaa tgtcaacgac cgaccttgag gcctacttca    480
aagactgtgt gtttaaggac tgggaggagc tgggggagga gattaggtta atgatctttg    540
tattaggagg ctgtaggcat aaattggtct gcgcaccagc accatgcaac ttttcacct     600 ctgcctaatc atctcttgta catgtcccac tgttcaagcc tccaagctgt gccttgggtg    660
gctttggggc atggacattg acccttataa agaatttgga gctactgtgg agttactctc    720 gttttttgcct tctgacttct ttccttccgt cagagatctc ctagacaccg cctcagctct    780
gtatcgagaa gccttagagt ctcctgagca ttgctcacct caccatactg cactcaggca    840
agccattctc tgctgggggg aattgatgac tctagctacc tgggtgggta ataatttgga    900
agatccagca tccagggatc tagtagtcaa ttatgttaat actaacatgg gtttaaagat    960
```

<210> SEQ ID NO 5
<211> LENGTH: 960
<212> TYPE: DNA
<213> ORGANISM: Hepatitis B virus

<400> SEQUENCE: 5

```
cgcatgcgtg gaacctttgt ggctcctctg ccgatccata ctgcggaact cctagccgct     60
```

| | |
|---|---|
| tgttttgctc gcagccggtc tggagcaaaa ctcatcggga ctgacaattc tgtcgtcctt | 120 |
| tctcggaaat atacatcctt cccatggctg ctaggttgta ctgccaactg gattcttcga | 180 |
| gggacgtcct ttgtctacgt cccgtcggcg ctgaatcccg cggacgaccc ctcgcgaggt | 240 |
| cgcttgggac tctatcgtcc ccttctccgt ctgccgtacc gtccgaccac ggggcgcacc | 300 |
| tctctttacg cggtctcccc gtctgtgcct tctcatctgc cggtccgtgt gcacttcgct | 360 |
| tcacctctgc acgttgcatg gagaccaccg tgaacgccca tcagatcctg cccaaggtct | 420 |
| tatataagag gactcttgga ctcccagcaa tgtcaacgac cgaccttgag gcctacttca | 480 |
| aagactgtgt gtttaaagac tgggaggagt tgggggagga gattaggtta aaggtttatg | 540 |
| tattaggagg ctgtaggcat aaaattggtct gcgcaccatc atcatgcaac ttttcacct | 600 |
| ctgcctaatc atctcttgta catgtcccac ttttcaagcc tccaagctgt gccttgggtg | 660 |
| gctttggggc atggacattg acccttataa agaatttgga gctacagtgg agttactctc | 720 |
| gtttttgcct tctgacttct ttccttccgt ccgggatcta ctagatacag cctcagctct | 780 |
| gtatcgggaa gcattagagt ctcctgagca ttgctcacct caccatacag cactcaggca | 840 |
| agccattctc tgctgggggg atgtactgga tctatctacc tgggtgggtg ctaatttgca | 900 |
| agatccagca tccagggatc tagtagtcaa ttatgttaat actaacatgg gcctaaagtt | 960 |

<210> SEQ ID NO 6
<211> LENGTH: 960
<212> TYPE: DNA
<213> ORGANISM: Hepatitis B virus

<400> SEQUENCE: 6

| | |
|---|---|
| cgcatgcgtg gaacctttgt gtctcctctg ccgatccata ctgcggaact cctagccgct | 60 |
| tgttttgctc gcagcaggtc tggggcaaaa ctcatcggga ctgacaattc tgtcgtgctc | 120 |
| tcccgcaagt atacatcgtt cccatggctg ctaggctgtg ctgccaactg gatcctgcgc | 180 |
| gggacgtcct ttgtttacgt cccgtcggcg ctgaatcccg cggacgaccc ctcccggggc | 240 |
| cgcttggggc tctaccgccc gcttctccgc ctgttgtacc gtccgaccac ggggcgcacc | 300 |
| tctctttacg cggactcccc gtctgtgcct tctcatctrc ggaccgtgt gcacttcgct | 360 |
| tcacctctgc acgtcgcatg gagaccaccg tgaacgccca ccggaacctg cccaaggtct | 420 |
| tgcataagag gactcttgga cttttcmgcaa tgtcaacgac cgaccttgag gcatacttca | 480 |
| aagactgtgt gtttaatgag tgggaggagt tgggggagga gaktaggtta aaggtctttg | 540 |
| tactaggagg ctgtaggcat aaaattggtgy gttcaccagc accatgcaac ttttcacct | 600 |
| ctgcctaatc atctcatgtt catgtcctac tgttcaagcc tccaagctgt gccttgggtg | 660 |
| gctttagggc atggacattg acccgtataa agaatttgga gcttctgtgg agttactctc | 720 |
| ttttttgcct catgacttct ttccttctat tcgagatctc ctcgacaccg cctctgcttt | 780 |
| gtatcgggag gccttagagt ctccggaaca ttgttcacct caccatacgg cactcaggca | 840 |
| agctattctg tgttggggtg agttgatgaa tctagccacc tgggtgggaa gtaatttgga | 900 |
| agatccagca tccagggaat tagtcgttag ctatgtcaac gttaatatgg gcmtaaaaat | 960 |

<210> SEQ ID NO 7
<211> LENGTH: 960
<212> TYPE: DNA
<213> ORGANISM: Hepatitis B virus

<400> SEQUENCE: 7

| | |
|---|---|
| cgcatgcgtg gaacctttgt gtctcctctg ccgatccata ctgcggaact cctagccgct | 60 |

-continued

| | |
|---|---|
| tgttttgctc gcagcaggtc tggagcgaaa ctcatcggga ctgacaattc tgtcgtgctc | 120 |
| tcccgcaagt atacatcgtt tccatggctg ctaggctgtg ctgccaactg gatcctgcgc | 180 |
| gggacgtcct ttgtttacgt cccgtcggcg ctgaatcccg cggacgaccc ctcccggggc | 240 |
| cgcttggggc tctaccgccc gcttctccgt ctgccgtacc gaccgaccac ggggcgcacc | 300 |
| tctctttacg cggactcccc gtctgtgcct tctcgtctgc cggaccgtgt gcacttcgct | 360 |
| tcacctctgc acgtcgcatg gaaaccaccg tgaacgccca ccggaacctg cccaaggtct | 420 |
| tgcacaagag gactcttgga ctttcagcaa tgtcaacgac cgaccttgag gcatacttca | 480 |
| aagactgtgt gtttcatgag tgggaggagc tgggggagga gattaggtta aaggtctttg | 540 |
| tactaggagg ctgtaggcat aaattggtct gttcaccagc accatgcaac tttttcacct | 600 |
| ctgcctagtc atctcttgtt catgtcctac tgttcaagcc tccaagctgt gccttgggtg | 660 |
| gctttgggac atggacattg acccttataa agaatttgga gctactgtgg agttactctc | 720 |
| tttttttgcct tctgacttct ttccgtcggt acgagacctc ctagataccg ctgctgctct | 780 |
| gtatcgggaa gccttagaat ctcctgaaca ttgctcacct caccacacag cactcaggca | 840 |
| agctattctg tgctgggggg aattaatgac tctagctacc tgggtgggta ataatttaga | 900 |
| agatccagcg tccagggatc tagtagtcaa ttatgttaac actaacatgg gcctaaagat | 960 |

<210> SEQ ID NO 8
<211> LENGTH: 960
<212> TYPE: DNA
<213> ORGANISM: Hepatitis B virus

<400> SEQUENCE: 8

| | |
|---|---|
| cgcatgcgtg ggacctttgt gtctcctctg ccgatccata ctgcggaact cctagccgct | 60 |
| tgttttgctc gcagcaggtc tggagcgaaa cttatcggga ctgacaattc cgttgtcctt | 120 |
| tcccgcaaat atacatcgtt tccatggctg ctaggctgtg ctgccaactg gatcctgcgc | 180 |
| gggacgtcct ttgtctacgt cccgtcggcg ctgaatcccg cggacgaccc ctcccggggc | 240 |
| cgcttggggc tctaccgccc gcttctccgt ctgccgtacc gaccgaccac ggggcgcacc | 300 |
| tctctttacg cggactcccc gtctgtgcct tctcgtctgc cggaccgtgt gcacttcgct | 360 |
| tcacctctgc acgtcgcatg gagaccaccg tgaacgccca ccggaacttg cccaaggtct | 420 |
| tgcataagag gactcttgga ctttcagcaa tgtcaacgac cgaccttgag gcatacttca | 480 |
| aagactgtgt gtttaatgag tgggaggagt gggggagga gattaggtta aaggtctttg | 540 |
| tactaggagg ctgtaggcat aaattggtct gttcaccagc accatgcaac tttttcacct | 600 |
| ctgcctaatc atctcatgtt catgtcctac tgttcaagcc tccaagctgt gccttgggtg | 660 |
| gctttggggc atggacattg acccgtataa agaatttgga gcttctgtgg agttactctc | 720 |
| tttttttgcct tctgacttct ttccttctat tcgagatctt ctcgacaccg cctctgctct | 780 |
| gtatcgggag gccttagagt ctccggaaca ttgttcacct caccatacgg cactcaggca | 840 |
| agctattctg tgttggggtg agttaatgaa tctagccacc tgggtgggaa gtaatttgga | 900 |
| agacccagca tccagggaat tagtagtcag ctatgtcaat gttaatatgg gcctaaaaat | 960 |

<210> SEQ ID NO 9
<211> LENGTH: 960
<212> TYPE: DNA
<213> ORGANISM: Hepatitis B virus

<400> SEQUENCE: 9

```
cgcatgcgtg gaacctttgt gtctcctctg ccgatccata ctgcggaact cctagccgct      60
tgttttgctc gcagcaggtc tggagcaaaa ctcatcggga ctgacaattc tgtcgtgctc     120
tcccgcaagt atacatcatt tccatggctg ctaggctgtg ctgccaactg gatcctgcgc     180
gggacgtcct ttgtttacgt cccgtcggcg ctgaatcccg cggacgaccc ctcccggggc     240
cgcttggggc tctaccgccc gcttctccgc ctgttgtacc gaccgaccac ggggcgcacc     300
tctctttacg cggactcccc gtctgtgcct tctcatctgc cggaccgtgt gcacttcgct     360
tcacctctgc acgtcgcatg gagaccaccg tgaacgccca ccggaacctg cccaaggtct     420
tgcataagag gactcttgga ctttcagcaa tgtcaacgac cgaccttgag gcatacttca     480
aagactgtgt gtttactgag tgggaggagt tgggggagga gattaggtta aaggtctttg     540
tactaggagg ctgtaggcat aaattggtgt gttcaccagc accatgcaac ttttttcacct     600 ctgcctaatc atctcatgtt catgtcctac tgttcaagcc tccaagctgt gccttgggtg     660
gctttggggc atggacattg acccgtataa agaatttgga gcttctgtgg agttactctc     720 tttttttgcct tctgacttct ttccttctat tcgagatctc ctcgacaccg cctctgctct     780
gtatcgggag gccttagagt ctccggaaca ttgttcacct caccatacgg cactcaggca     840
agctattctg tgttggggtg agttaatgaa tctagccacc tgggtgggaa gtaatttgga     900
agatccagca tccagggaat tagtagtcag ctatgtcaac gttaatatgg gcctaaaaat     960
```

<210> SEQ ID NO 10
<211> LENGTH: 960
<212> TYPE: DNA
<213> ORGANISM: Hepatitis B virus

<400> SEQUENCE: 10

```
cgcatgcgtg gaacctttgt ggctcctctg ccgatccata ctgcggaact cctagcagct      60
tgttttgctc gcagccggtc tggagctaaa cttatcggga ctgacaactc tgttgtcctc     120
tcgcggaaat acacctcctt cccatggctg ctcgggtgtg ctgccaactg gatcctgcgc     180
gggacgtcct ttgtctacgt cccgtcggcg ctgaatcccg cggacgaccc atctcggggc     240 cgtttggggcc tctaccgtcc ccttcttcac ctgccgttcc agccgaccac ggggcgcacc     300
tctctttacg cggactcccc gtctgtgcct tctcatctgc cggaccgtgt gcacttcgct     360
tcacctctgc acgtcgcatg gagaccaccg tgaacgccca ccaggtcttg cccaagctct     420
tacataagag gactcttgga ctctcagcaa tgtcaacgac cgaccttgag gcatacttca     480
aagactgttt gtttaaagac tgggaggagt tgggggagga gattaggtta aaggtctttg     540
tactaggagg ctgtaggcat aaattggtct gttcaccagc accatgcaac ttttttcccct     600 ctgcctaatc atctcatgtt catgtcctac tgttcaagcc tccaagctgt gccttgggtg     660
gctttggggc atggacattg acccgtataa agaatttgga gcttctgtgg agttactctc     720 tttttttgcct tctgacttct ttccttctat tcgagatacccg cctctgctct     780 gtatcgggag gccttagagt ctccggaaca ttgttcacct caccatacag cactcaggca     840
agctattctg tgttggggtg agttgatgaa tctggccacc tgggtgggaa gtaatttgga     900
agacccagca tccagggaat tagtagtcag ctatgtcaat gttaatatgg gcctaaaaat     960
```

<210> SEQ ID NO 11
<211> LENGTH: 961
<212> TYPE: DNA
<213> ORGANISM: Hepatitis B virus

<400> SEQUENCE: 11

```
cgcatgcgtg gaacctttgt ggctcctctg ccgatccata ctgcggaact cctagcggct      60
twgttttgct cgcagccggt ctggagcgaa cctcatcggc accgacaact ctgttgtcct     120
ctctcggaag tacacctcct ttccatggct gctaggatgt gctgccaact ggatcctgcg     180
cgggacgtcc tttgtctacg tcccgtcggc gctgaatccc gcggacgacc cctctcgggg     240
ccgcttgggg atctaccgtc ccctcctccg tctgccgttc cggccgacca cggggcgcac     300
ctctctttac gcggtctccc cgtctgtgcc ttctcatctg ccggaccgtg tgcacttcgc     360
ttcacctctg cacgtcgcat ggagaccacc gtgaacgccc accaggtctt gcccaaggtc     420
ttgcataaga ggactcttgg actctcagca atgtcaacga ccgaccttga gcatacttc      480
aaagactgtg tgtttaaaga ctgggaggag ttgggggagg agattaggtt aaaggtcttt     540
gtactaggag gctgtaggca taaattggtc tgttcaccag caccatgcaa cttttttcacc    600
tctgcctaat catctcatgt tcatgtccta ctgttcaagc ctccaagctg tgccttgggt     660
ggctttgggg catggacatt gaccccttata aagaatttgg agcttctgtg gagttactct    720
cttttttgcc gtctgatttc tttccatcta ttcgagatct cctagacact gcctcagctc    780
tgtatcggga agccttagag tctccggaac attgttcacc tcaccataca gcactcaggc    840
aagctgttct gtgttggggt gaattaatga atctggctac ctgggtggga agtaatttgg    900
aagatccagc atccagggaa ttagtagtca gttatgtcaa tgttaatatg gcttaaaga    960
t                                                                    961

<210> SEQ ID NO 12
<211> LENGTH: 960
<212> TYPE: DNA
<213> ORGANISM: Hepatitis B virus

<400> SEQUENCE: 12
cgcatgcgtg gaacctttgt ggctcctctg ccgatccata ctgcggaact cctggcagct      60
tgttttgctc gcagccggtc tggagcgaaa cttatcggga ctgacaactc tgttgtcctt    120
tctcggaaat acacctcctt cccatggctg ctcggatgtg ctgccaactg gatcctgcgc    180
gggacgtcct ttgtctacgt cccgtcggcg ctgaatcccg cggacgaccc gtctcggggc    240
cgtttgggcc tctaccgtcc ccttctgcag ctgccgttcc ggccgaccac ggggcgcacc    300
tctctttacg cggtctcccc gtctgtgcct tctcatctgc cggaccgtgt gcacttcgct    360
tcacctctgc acgtcgcatg gagaccaccg tgaacgccca ccaggtcttg cccaaggtct    420
tacataagag gactcttgga ctctcagcaa tgtcaacgac cgaccttgag gcatacttca   480
aagactgttt gtttaaagac tgggaggagt tgggggagga gattaggtta aaggtctttg    540
tactaggagg ctgtaggcat aaattggtct gttcaccagc accatgcaac ttttcacct    600
ctgcctaatc atctcatgtt catgtcccac tgttcaagcc tccaagctgt gccttgggtg    660
gctttggggc atggacattg acccgtataa agaatttgga gcttctgtgg agttactctc    720
ttttttgcct tctgacttct tccttctat tcgagatctc ctcgacaccg cctctgcact    780
gtatcgggag gccttagagt ctccggaaca ttgttcacct caccatacag cactcaggca    840
agctattctg tgttggggtg agttgatgaa tctggccacc tgggtgggaa gtaatttgga    900
agacccagca tccagggaat tagtagtcag ctatgtcaat gttaacatgg cctaaaaat    960

<210> SEQ ID NO 13
<211> LENGTH: 960
<212> TYPE: DNA
```

<213> ORGANISM: Hepatitis B virus

<400> SEQUENCE: 13

```
cgcatgcgtg gaacctttgt ggctcctctg ccgatccata ctgcggaact cctagcagct    60
tgttttgctc gcagccggtc tggagcgaaa cttatcggca ccgacaactc tgttgtcctc   120
tctcggaaat acacctcctt tccatggctg ctaggtgtg ctgccaactg gatcctgcgc    180
gggacgtcct ttgtctacgt cccgtcggcg ctgaatcccg cggacgaccc gtctcggggc   240
cgtttgggac tctaccgtcc ccttcttcat ctgccgttcc ggccgaccac ggggcgcacc   300
tctctttacg cggtctcccc gtctgtgcct tctcatctgc cggaccgtgt gcacttcgct   360
tcacctctgc acgtcgcatg gagaccaccg tgaacgccca ccaggtcttg cccaaggtct   420
tacataagag gactcttgga ctctcagcaa tgtcaacgac cgaccttgag gcatacttca   480
aagactgttt gtttaaagac tgggaggagt tgggggagga gattaggtta atgatctttg   540
tactaggagg ctgtaggcat aaattggtct gttcaccagc accatgcaac ttttcaccct   600
ctgcctaatc atctcatgtt catgtcctac tgttcaagcc tccaagctgt gccttgggtg   660
gctttggggc atggacattg acccgtataa agaatttgga gcttctgtgg agttactctc   720
tttttttgcct tctgacttct ttccttctat tcgagatctc ctcgacaccg cctctgctct   780
gtatcgggag gccttagagt ctccggaaca ttgttcacct caccatacag cactcaggca   840
agctattctg tgttggggtg agttgatgaa tctggccacc tgggtgggaa gtaatttgga   900
agacccagca tccagggaat tagtagtcag ctatgtcaat gttaatatgg gcctaaaaat   960
```

<210> SEQ ID NO 14
<211> LENGTH: 960
<212> TYPE: DNA
<213> ORGANISM: Hepatitis B virus

<400> SEQUENCE: 14

```
cgcgtgcgtg gaaccttttc ggctcctctg ccgatccata ctgcggaact cctagccgct    60
tgttttgctc gcagcaggtc tggagcaaac attatcggga ctgataactc tgttgtcctc   120
tcccgcaaat atacatcgta tccatggctg ctaggctgtg ctgccaactg gatcctgcgc   180
gggacgtcct ttgtttacgt cccgtcggcg ctgaatcctg cggacgaccc ttctcggggt   240
cgcttgagac tctctcgtcc ccttctccgt ctgccgttcc gaccgaccac ggggcgcacc   300
tctctttacg cggactcccc gtctgtgcct tctcatctgc cggaccgtgt gcacttcgct   360
tcacctctgc acgtcgcatg gagaccaccg tgaacgccca ccgaatgttg cccaaggtct   420
tacataagag gactcttgga ctctctgcaa tgtcaacgac cgaccttgag gcatacttca   480
aagactgttt gtttaaagac tgggaggagt tgggggagga gattagatta aaggtctttg   540
tactaggagg ctgtaggcat aaattggtct gcgcaccggc gccatgcacc ttttcaccct   600
ctgcctaatc atctcttgtt catgtcctac tgttcaagcc tccaagctgt gccttgggtg   660
gctttggggc atggacatcg acccttataa agaatttgga gctactgtgg agttactctc   720
gtttttgcct tctgacttct ttccttcagt acgagatctt ctagataccg cctcagctct   780
gtatcgggaa gccttagagt ctcctgagca ttgttcacct caccatactg cactcaggca   840
agcaattctt tgctgggggg aactaatgac tctagctacc tgggtgggtg ttaatttgga   900
agatccagca tctagagacc tagtagtcag ttatgtcaac actaatatgg gcctaaagtt   960
```

<210> SEQ ID NO 15
<211> LENGTH: 960

<212> TYPE: DNA
<213> ORGANISM: Hepatitis B virus

<400> SEQUENCE: 15

```
cgcatgcgtg gaaccttttt ggctcctctg ccgatccata ctgcggaact cctagccgct      60
tgttttgctc gcagcaggtc tggagcaaac attctcggga ctgacaactc tgttgtcctc     120
tcccgcaaat atacatcgtt tccatggctg ctaggctgtg ctgccaactg gatcctgcgc     180
gggacgtcct ttgtttacgt cccgtcgrcg ctgaatcccg cggacgaccc gtctcggggc     240
cgcttggggc cctgtcgtcc tcttctctgc ctgccgttcc gaccgagcac ggggcgcacc     300
tctctttacg cggactcccc gtctgtgcct tctcatctgc cggaccgtgt gcacttcgct     360
tcacctctgc acgtcgcatg gagaccaccg tgaacgccca ccaaagcttg cccaaggtct     420
tacataagag gactcttgga ctctctgcaa tgtcaacgac cgaccttgag catacttca      480
aagactgttt gtttaacgac tgggaggagt tgggggagga gattaggtta aaggtctttg     540
tactaggagg ctgtaggcat aaattggtct gcgcaccagc accatgcaac ttttcacct      600
ctgcctaatc atcttttgtt catgtcctac tgttcaagcc tccaagctgt gccttgggtg     660
gctttagggc atggacattg acccttataa agaatttgsa gcttctgtgc agttactctc     720
gttttttgcct gttsacttct ttccttccgt acgagatctt ctagataccg cctcagctct     780
gtatcgggat gctttagagt ctcctgagca tttgtcaccg caccatactg cactcaggca     840
agcaattctt tgctggggag aattaatgac tctagctacc tgggtgggta ctaatttaga     900
agatcaagca tctagggacc tagtagtcag ttatgtcaac amtaatatgg gcctaaagtt     960
```

<210> SEQ ID NO 16
<211> LENGTH: 957
<212> TYPE: DNA
<213> ORGANISM: Hepatitis B virus

<400> SEQUENCE: 16

```
cgcatgcgtg gaacctttgt ggctcctctt ccgatccata ctgcggaact cctagccgct      60
tgttttgctc gcagccggtc tggagcaaac attattggga ctgataactc tgttgtcctc     120
tcccgcaaat atacatcgtt tccatggctg ctaggccgtg ctgccaactg ggtcctgcgc     180
gggacgtcct ttgtttacgt cccgtcggcg ctgaatcccg cggacgaccc ttctcggggt     240
cgcttgggac tctctcgtcc ccttctccgt ctgccgttcc gaccgaccac ggggcgcacc     300
tctctttacg cggactcccc gtctgtgcct tctcatctgc cggaccgtgt gcacttcgct     360
tcacctctgc acgtcgcatg gagaccaccg tgaacgccca ccaattgccc aaggtcttac     420
ataagaggac tcttggactc tctgcaatgt caacgaccga ccttgaggca tacttcaaag     480
actgtttgtt taaagactgg gagagttgg gggaggagat tagattaaag gtctttgtac     540
taggaggctg taggcataaa ttggtctgcg caccagcacc atgcaacttt tcacctctg      600
cctaatcatc tcttgttcat gtcctactgt tcaagcctcc aagctgtgcc ttgggtggct     660
ttggggcatg gacattgacc cttataaaga atttggagct accgtggagt tactctcatt     720
tttgccttct gacttctttc cttcggtacg agatcttcta gataccgcct cagctctgta     780
tcgggaagct ttagagtctc ttgagcattg ttcacctcac catactgcac tcaggcaagc     840
aattctttgc tgggggaac taatgactct agctacctgg gtgggagtta atttggaaga     900
tccagcatct agggacctag tagtcagtta tgtcaacact aatatgggcc taaagtt       957
```

<210> SEQ ID NO 17

```
<211> LENGTH: 960
<212> TYPE: DNA
<213> ORGANISM: Hepatitis B virus

<400> SEQUENCE: 17
cgcatgcgtg gaacctttgt ggctcctctg ccgatccata ctgcggaact cctagccgct        60
tgttttgctc gcagcaggtc tggagcraaa cttatcggga cggataattc tgtcgtcctc       120
tcccggaaat atacatcgtt tccatggctg ctaggctgtg ctgccaactg gatcctgcga       180
gggacgtcct ttgtctacgt cccgtcggcg ctgaatcctg cggacgaccc gtctcggggt       240
cgcttggggg tctatcgtcc ccttctccgt ctrccgttcc agccgwccac ggggcgcacc       300
tctctttacg cggtctcccc gtctgtgcct tctcgcctgc cggwccgtgt gcacttcgct       360
tcacctctgc acgtcgcatg gagaccaccg tgaacgccca ccagatattg cccaaggtct       420
tatataagag gactcttgga ctctctgcaa tgtcaacgac cgaccttgag gcatacttca       480
aagactgttt gtttaaagac tgggaggagt tgggggagga gattagatta atgatctttg       540
tactaggagg ctgtaggcat aaawtggtct gcgtaccagc accatgcaac ttttcaccct       600
ctgcctaatc atctcgtgtt catgtcctac tgttcaagcc tccaagctgt gccttgagtg       660
gctttaggac atggacattg acccttataa agaatttgga gcttctgtgg agttactctc       720
gttttttgcct tctgacttct ttccttcagt aagagatctt ctagataccg cctctgctct       780
gtttcgggat gccttagaat ctcctgagca ttgttcacct caccatactg cactcaggca       840
agccattctt tgctggggag atgtaatgaa tctagctaca tgggtgggtg caaatttgga       900
agatccaaca tccagggacc tggtagtcgg ttatgtcaat agtaatatgg gcctaaagtt       960

<210> SEQ ID NO 18
<211> LENGTH: 960
<212> TYPE: DNA
<213> ORGANISM: Hepatitis B virus

<400> SEQUENCE: 18
cgcatgcgtg gaacctttgy ggctcctctg ccgatccata ctgcggaact cctggccgct        60
tgttttgctc gcagcaggtc tggagcgaaa cttattggaa cggataattc tgtcgttctc       120
tcccggaaat atacatcatt tccatggctg ctaggctgtg ctgccaactg gatcctgcga       180
gggacgtcct ttgtctacgt cccgtcagcg ctgaatcctg cggacgaccc gtctcggggt       240
cgcttgggga tctatcgtcc ccttctccgt ctgccgttcc ggccgaccac ggggcgcacc       300
tctctttacg cggtctcccc gtctgtgcct tctcatctgc cggaccgtgt gcacttcgct       360
tcacctctgc acgtcgcatg gaaaccaccg tgaacgccca caaatcttg cccaaggtct       420
tatataagag gactcttgga ctctctgcaa tgtcaacgac cgaccttgag gcatacttca       480
aagactgctt gtttaaagac tgggaggagt tgggggagga gattagatta atgatctttg       540
tactaggagg ctgtaggcat aaattggtct gcgcaccagc accatgcaac ttttcaccct       600
ctgcctaatc atctcttgtt catgtcctac tgttcaagcc tccaagctgt gccttgggtg       660
gctttaggac atggacattg acccttataa agaatttgga gctwctgtgg agttactctc       720
kttttttgcct catgacttct ttccttcaat aagagatctt ctagataccg ccacagctct       780
gtatcgggat gccttagaat ctcctgagca ttgttcacct caccacacgg cactcaggca       840
agccattctt tgctgggggg atgtaatgaa tctagctacc tgggtgggtg taaatttgga       900
agatccagca tccagggacc tggtagtcgg ttatgtcaat actaatatgg gcctaaagtt       960
```

```
<210> SEQ ID NO 19
<211> LENGTH: 960
<212> TYPE: DNA
<213> ORGANISM: Hepatitis B virus

<400> SEQUENCE: 19
cgcatgcgtg gaacctttgt ggctcctctg ccgatccata ctgcggaact cctagccgct     60
tgttttgctc gcagcaggtc tggagcgaaa ctcataggga cagataattc tgtcgttctc    120
tcccggaaat atacatcatt tccatggctg ctaggctgtg ctgccaactg gatcctgcga    180
gggacgtcct ttgtctacgt cccgtcagcg ctgaatcctg cggacgaccc ctctcggggc    240
cgcttggggg tctatcgtcc ccttctccgt ctgccgttcc ggccgaccac ggggcgcacc    300
tctctttacg cggtctcccc gtctgtgcct tctcatctgc cggaccgtgt gcacttcgct    360
tcacctctgc acgtcgcatg gagaccaccg tgaacgccca ccagatcttg cccaaggtct    420
tacataagag gactcttgga ctctctgcaa tgtcaacgac cgaccttgag gcatacttca    480
aagactgttt gtttaaagac tgggaggagt tgggggagga actagattaa tgatctttg     540 tactaggagg ctgtaggcat aaattggtct gcgcaccagc accatgcaac ttttcacct    600 ctgcctaatc atctcttgtt catgtcctac tgttcaagcc tccaagctgt gccttgggtg    660
gctttgggac atggacattg acccttataa agaatttgga gctactgtgg agttactctc    720 gttttttgcct tctgacttct ttccttcagt aagagatctt ctagataccg cctctgctct    780
gtatcgggat gccttagaat ctcctgagca ttgttcacct caccatactg cactcaggca    840
agccattctt tgctggggag aattaatgac tctagctacc tgggtgggtg taaatttgga    900
agatccagca tccagggacc tagtagtcag ttatgtcaat actaatatgg gcctaaagtt    960

<210> SEQ ID NO 20
<211> LENGTH: 960
<212> TYPE: DNA
<213> ORGANISM: Hepatitis B virus

<400> SEQUENCE: 20
cgcatgcgtg gaacctttgt ggctcctctg ccgatccata ctgcggaact ccttgcagct     60
tgtttcgctc gcagccggtc tggagcgaaa ctcatcggca cagacaactc tgttgtcctc    120
tctaggaagt acacctcctt cccatggctg ctcggttgtg ctgccaactg gatcctacgc    180
gggacgtcct ttgtttacgt cccgtcgcgc ctgaatccag cggacgatcc ctctcggggt    240
cgcttggggc tgtatcgccc ccttctccgt ctgccgttcc agccgacgac gggtcgcacc    300
tctctttacg cggcctcccc gtctgttcct tctcgtctgc cggaccgtgt gcacttcgct    360
tcacctctgc acgtcgcatg gagaccaccg tgaacgcccc tcgaagcttg ccaacagtct    420
tacataagcg gactcttgga cttcaggaa ggtcaatcac ctggatcgaa gaatacatca    480
aagactgtgt atttaaggac tgggaggagc tgggggagga gattaggtta aggtctttg     540 tattaggagg ctgtaggcat aaattggtct gttcaccagc accatgcaac ttttcacct    600 ctgcctaatc atcttttgtt catgtcctac tgttcaagcc tccaagctgt gccttgggtg    660
gctttggggc atggacattg acccttataa agaatttgga gcttctgtgg aattactctc    720 tttttttgcct tctgacttct tcccgtcagt tcgggaccta ctcgacaccg cttcagccct    780
ctaccgggat gctttagaat caccagaaca ttgcacacct aaccataccg ctctcaggca    840
agctatattg tgctgggggtg agttaatgac tttggcttcc tgggtgggca ataacttgga    900
agatcctgct gctagggacc tagtggttaa ctatgtcaat actaacatgg gcctaaaaat    960
```

<210> SEQ ID NO 21
<211> LENGTH: 960
<212> TYPE: DNA
<213> ORGANISM: Hepatitis B virus

<400> SEQUENCE: 21

```
cgcatgcgtg gaacctttgt ggctcctctg ccgatccata ctgcggaact ccttgcagcc      60
tgtttcgctc gcagccggtc tggagcgaac attatcggca cagacaactc tgttgtcctc     120
tctaggaagt acacctcctt tccatggctg ctcggttgtg ctgccaactg gatcctgcgc     180
gggacgtcct ttgtttacgt cccgtcggcg ctgaatcccg cggacgaccc ttcccggggt     240
cgcttggggc tgtaccgccc ccttcttcgt ctgccgttcc agccgacgac gggtcgcacc     300
tctctttacg cggactcccc gtctgttcct tctcatctgc cggaccgtgt gcacttcgct     360
tcacctctgc acgtcgcatg gagaccaccg tgaacgcccc ctggaatctg ccaacagtct     420
tacataagag gactcttgga ctttcaggac ggtcaatgac ctggatcgaa gaatacatca     480
aagactgtgt atttaaggac tgggaggagc tgggggagga gatcaggtta aaggtctttg     540
tactaggagg ctgtaggcat aaattggtct gttcaccagc accatgcaac ttttcacct      600
ctgcctaatc atcttttgtt catgtcccac tgttcaagcc tccaagctgt gccttgggtg     660
gctttggggc atggacattg acccttataa agaatttgga gcttctgtgg aattgctctc     720
tttttttgcct tctgatttct tcccgtctgt tcgggaccta ctcgacaccg cttcagccct     780
ttaccgggat gctctagagt caccggaaca ttgcaccccc aatcataccg ctctcaggca     840
agctattttg tgctggggtg agttaatgac tttggcttcc tgggtgggta ataatttgga     900
agaccctgca gctagggatt tagtagttaa ttatgtcaac actaatatgg gcctgaaaat     960
```

<210> SEQ ID NO 22
<211> LENGTH: 960
<212> TYPE: DNA
<213> ORGANISM: Hepatitis B virus

<400> SEQUENCE: 22

```
cgcatgcgtg gaacctttgt ggctcctctg ccgatccata ctgcggaact ccttgcagcc      60
tgtttcgctc gcagccggtc tggagcgaac attatcggca cagacaactc tgttgtcctc     120
tctaggaagt acacctcctt tccatggctg ctcggttgtg ctgccaactg gatcctgcgc     180
gggacgtcct ttgtttacgt cccgtcggcg ctgaatcccg cggacgaccc ttcccggggt     240
cgcttggggc tctaccgccc ccttcttcgt ctgccgttcc agccgacgac gggtcgcacc     300
tctctttacg cggactcccc gtctgttcct tctcatctgc cggaccgtgt gcacttcgct     360
tcacctctgc acgtcgcatg gagaccaccg tgaacgcccc ctggaatctg ccaacagtct     420
tacataagag gactcttgga ctttcaggac ggtcaatgac ctggatcgaa gaatacatca     480
aagactgtgt atttaaggac tgggaggagc tgggggagga gatcaggtta aaggtctttg     540
tactaggagg ctgtaggcat aaattggtct gttcaccagc accatgcaac ttttcacct      600
ctgcctaatc atcttttgtt catgtcccac tgttcaagcc tccaagctgt gccttgggtg     660
gctttggggc atggacattg acccttataa agaatttggc gcttctgtgg aattgctctc     720
tttttttgcct tctgatttct tcccgtctgt tcgggaccta ctcgacaccg cttcagccct     780
ttaccgggat gctctagagt caccggaaca ttgcaccccc aatcataccg ctctcaggca     840
agctattttg tgctggggtg agttaatgac tttggcttcc tgggtgggta ataatttgga     900
agaccctgca gctagggatt tagtagttaa ttatgtcaac actaatatgg gcctgaaaat     960
```

<210> SEQ ID NO 23
<211> LENGTH: 996
<212> TYPE: DNA
<213> ORGANISM: Hepatitis B virus

<400> SEQUENCE: 23

| | | | | | | |
|---|---|---|---|---|---|---|
| cgcatgcgtg | gaacctttgt | ggctcctctg | ccgatccata | ctgcggaact | cctagctgct | 60 |
| tgttttgctc | gcagccggtc | tggagcaaaa | ctcattggga | ctgacaattc | tgtcgtcctt | 120 |
| tctcggaaat | atacatcctt | tccatggctg | ctaggctgtg | ctgccaactg | gatccttcgc | 180 |
| gggacgtcct | ttgtttacgt | cccgtcagcg | ctgaatccag | cggacgaccc | ctcccggggc | 240 |
| cgtttggggc | tctgtcgccc | ccttctccgt | ctgccgttcc | tgccgaccac | ggggcgcacc | 300 |
| tctctttacg | cggtctcccc | gtctgttcct | tctcatctgc | cggaccgtgt | gcacttcgct | 360 |
| tcacctctgc | acgttacatg | gaaaccgcca | tgaacacctc | tcatcatctg | ccaaggcagt | 420 |
| tatataagag | gactcttgga | ctgtttgtta | tgtcaacaac | cggggtggag | aaatacttca | 480 |
| aggactgtgt | ttttgctgag | tgggaagaat | taggcaatga | gtccaggtta | atgacctttg | 540 |
| tattaggagg | ctgtaggcat | aaattggtct | gcgcaccagc | accatgtaac | ttttcacct | 600 |
| ctgcctaatc | atctcttgtt | catgtcctac | tgttcaagcc | tccaagctgt | gccttgggtg | 660 |
| gctttagggc | atggatagaa | caactttgcc | atatggcctt | tttggcttag | acattgaccc | 720 |
| ttataaagaa | tttggagcta | ctgtggagtt | gctctcgttt | ttgccttctg | acttttccc | 780 |
| gtctgttcgt | gatcttctcg | acaccgcttc | agctttgtac | cgggaatcct | tagagtcctc | 840 |
| tgatcattgt | tcgcctcacc | atacagcact | caggcaagca | atcctgtgct | ggggtgagtt | 900 |
| gatgactcta | gccacctggg | tgggtaataa | tttggaagat | ccagcatcca | gagatttggt | 960 |
| ggtcaattat | gttaatacta | atatgggttt | aaaaat | | | 996 |

<210> SEQ ID NO 24
<211> LENGTH: 996
<212> TYPE: DNA
<213> ORGANISM: Hepatitis B virus

<400> SEQUENCE: 24

| | | | | | | |
|---|---|---|---|---|---|---|
| cgcatgcgtg | gaacctttgt | ggctcctctg | ccgatccata | ctgcggaact | cctagctgct | 60 |
| tgttttgctc | gcagccggtc | tggagcaaaa | ctcattggga | ctgacaattc | tgtcgtcctt | 120 |
| tctcggaaat | atacatcctt | tccatggctg | ctaggctgtg | ctgccaactg | gatccttcgc | 180 |
| gggacgtcct | ttgtttacgt | cccgtcagcg | ctgaatccag | cggacgaccc | ctcccggggc | 240 |
| cgtttggggc | tctgtcgccc | ccttctccgt | ctgccgttcc | tgccgaccac | ggggcgcacc | 300 |
| tctctttacg | cggtctcccc | gtctgttcct | tctcatctgc | cggaccgtgt | gcacttcgct | 360 |
| tcacctctgc | acgttacatg | gaaaccgcca | tgaacacctc | tcatcatcta | ccaaggcagt | 420 |
| tatataagag | gactcttgga | ctgtttgtta | tgtcaacaac | cggatggag | aaatacttca | 480 |
| aggactgtgt | ttttgctgag | tgggaagaat | taggcaatga | gtccaggtta | atgacctttg | 540 |
| tattaggagg | ctgtaggcat | aaattggtct | gcgcaccagc | accatgtaac | ttttcacct | 600 |
| ctgcctaatc | atctcttgtt | catgtcctac | tgttcaagcc | tccaagctgt | gccttgggtg | 660 |
| gctttagggc | atggatagaa | caactttgcc | atatggcctt | tttggcttag | acattgaccc | 720 |
| ttataaagaa | tttggagcta | ctgtggagtt | gctctcgttt | ttgccttctg | acttttccc | 780 |
| gtctgttcgt | gatcttctcg | acaccgcttc | agctttgtac | cgggaatcct | tagagtcctc | 840 |

```
tgatcattgt tcgcctcacc atacagcact caggcaagca attctgtgct ggggtgagtt      900
gatgactcta gctacctggg tgggtaataa tttggaagat ccagcatcca gagatttggt      960
ggtcaattat gttaatacta atatgggttt aaaaat                                996

<210> SEQ ID NO 25
<211> LENGTH: 999
<212> TYPE: DNA
<213> ORGANISM: Hepatitis B virus

<400> SEQUENCE: 25
cgcatgcgtg aacctttgt ggctcctctg ccgatccata ctgcggaact cctagctgct       60
tgttttgctc gcagccggtc tggagcgaaa ctcattggga ctgacaattc tgtcgtcctt     120
tctcggaaat atacatcctt tccatggctg ctaggctgtg ctgccaactg gatccttcgc     180
gggacgtcct ttgtttacgt cccgtcagcg ctgaatccag cggacgaccc ctcccggggc     240
cgtttggggc tctgtcgccc ccttctccgt ctgccgttcc tgccgaccac ggggcgcacc     300
tctctttacg cggtctcccc gtctgttcct tctcatctgc cggaccgtgt gcacttcgct     360
tcacctctgc acgttacatg gaaaccgcca tgaacacctc tcatcatctg ccaaggcagt     420
tatataagag gactcttgga ctgtttgtta tgtcaacaac cggggtggag aaatacttca     480
aggactggtg tgttttttgct gagtgggaag aattaggcaa tgagtccagg ttaatgacct     540
ttgtattagg aggctgtagg cataaattgg tctgcgcacc agcaccaatg caacttttca     600
cctctgccta atcatctctt gttcatgtcc tactgttcaa gcctccaagc tgtgccttgg     660
gtggctttag gcatggata gaacaacttt gccatatggc cttttttggct tagacattga     720 cccttataaa gaatttggag ctactgtgga gttgctctcg ttttttgcctt ctgactttt      780 cccgtctgtt cgtgatcttc tcgacaccgc ttcagctttg taccgggaat ccttagagtc     840
ctctgatcat tgttcgcctc accatacagc actcaggcaa gcaatcctgt gctggggtga     900
gttgatgact ctagctacct gggtgggtaa taatttggaa gatccagcat ccagagattt     960
ggtggtcaat tatgttaata ctaatatggg tttaaaaat                            999

<210> SEQ ID NO 26
<211> LENGTH: 960
<212> TYPE: DNA
<213> ORGANISM: Hepatitis B virus

<400> SEQUENCE: 26
cgcatgcgcg aacctttgt ggctcctctg ccgatccata ctgcggaact cctagccgct       60
tgtttcgctc gcagcaggtc tggagcggac attatcggca ctgacaactc cgttgtcctt     120
tctcggaagt acacctcctt cccatggctg ctaggatgtg ctgccaactg gatcctgcgc     180
gggacgtcct ttgtctacgt cccgtcggcg ctgaatcctg cggacgaccc ctctcgtggt     240
cgcttggggc tctgccgccc tcttctccgc ctgccgttcc ggccgacgac gggtcgcacc     300
tctctttacg cggactcccc gcctgtgcct tctcatctgc cggcccgtgt gcacttcgct     360
tcacctctgc acgtcgcatg gagaccaccg tgaacgcccc ttggaacttg ccaacaacct     420
tacataagag gactcttgga ctttcgcccc ggtcaacgac ctggattgag aatacatca     480 aagactgtgt atttaaggac tgggaggagt cggggagga gttgaggtta aaggtctttg     540
tattaggagg ctgtaggcat aaattggtct gttcaccagc accatgcaac ttttcaccct     600
ctgcctaatc atcttttgtt catgtcccac tgttcaagcc tccaagctgt gccttgggtg     660
gctttggggc atggacattg acccttataa agaatttgga gcttctgtgg agttactctc     720
```

```
atttttgcct tctgacttct tcccgtctgt ccgggaccta ctcgacaccg cttcagccct    780
ctaccgagat gccttagaat caccagaaca ttgcacccc aaccacactg ctctcaggca     840
agctattttg cgctggggtg agttgatgac cttggcttcc tgggtgggca ataatttaga    900
ggatcctgca gcaagagatc tagtagttaa ttatgtcaat actaacatgg gcctaaaaat    960

<210> SEQ ID NO 27
<211> LENGTH: 960
<212> TYPE: DNA
<213> ORGANISM: Hepatitis B virus

<400> SEQUENCE: 27
cgcatgcgcg gaacctttgt ggctcctctg ccgatccata ctgcggaact cctagccgct     60
tgtttcgctc gcagcaggtc tggagcggac attatcggca ctgacaactc cgttgtcctt    120
tctcggaagt acacctcctt cccatggctg ctaggttgtg ctgccaactg atcctgcgc     180 gggacgtcct ttgtctacgt cccgtcggcg ctgaatcctg cggacgaccc ctctcgtggt    240
cgcttggggc tctgccgccc tcttctccgc ctgtcgttcc ggccgacgac gggtcgcacc    300
tctctttacg cggactcccc gcctgtgcct tctcatctgc cggcccgtgt gcacttcgct    360
tcacctctgc acgtcgcatg gagaccaccg tgaacgcccc ttggaacttg ccaacaacct    420
tacataagag gactcttgga cttctcgcccc ggtcaacgac ctggattgag gaatacatca   480
aagactgtgt atttaaggac tgggaggagt cggggggagga gttgaggtta aaggtctttg    540
tattaggagg ctgtaggcat aaattggtct gttcaccagc accatgcaac tttttcacct    600
ctgcctaatc atcttttgtt catgtcccac tgttcaagcc tccaagctgt gccttgggtg    660
gctttggggc atggacattg acccttataa agaatttgga gcttctgtgg agttactctc    720
atttttgcct tctgacttct tcccgtctgt ccgggaccta ctcgacaccg cttcagccct    780
ctaccgagat gccttagaat caccagaaca ttgcacccc aaccacactg ctctcaggca     840
agctattttg tgctggggtg agttgatgac attggcttcc tgggtgggca ataatttaga    900
ggatcctgca gcaagagatc tagtagttaa ttatgtcaat actaacatgg gcctaaaaat    960

<210> SEQ ID NO 28
<211> LENGTH: 960
<212> TYPE: DNA
<213> ORGANISM: Hepatitis B virus

<400> SEQUENCE: 28
cgcatgcgcg gaaccttta ggctccgctg ccgatccata ctgcggaact cctagcagct      60
tgtttcgctc gcagccggtc tggagcggac attatcggca ctgacaactc cgttgtcctt    120
tctcggaagt acacctcctt cccatggctg ctaggctgtg ctgccaactg atcctgcgc     180 gggacgtcct ttgtctacgt cccgtcggcg ctgaatcctg cggacgaccc ctctcgtggt    240
cgcttggggc tatgccgccc tcttctccgc ctgtcgttcc ggccgacgac gggtcgcacc    300
tctctttacg cggactcccc acctgtgcct ttacatcggc cggcccgtgt gcacttcgct    360
tcacctctgc acgtcgcatg gaaccaccg tgaacgcccc ttggaacttg ccaacaacct     420
tatataagag gactcttgga cttctcgcccc ggtcaacgac ctggattgag gaatacatca   480
aagactgtgt atttaaggac tgggaggagt cggggggagga gtcgaggtta atgatctttg    540
tattaggagg ctgtaggcat aaattggtct gttcaccagc accatgcaac tttttcacct    600
ctgcctaatc agcttttgtt catgtcctac tgttcaagcc tccaagctgt gccttgggtg    660
```

```
gctttgggac atggacatcg acccttataa agaatttgga gcttctgtgg agttactctc    720
mtttttgcct tctgatttct tcccgtctgt ccgggaccta ctcgacaccg cttcagccct    780
cttccgagat gccttagaat cacccgaaca ttgcaccccc caccayacag ctctcaggca    840
agctattttg tgctggggtg agttgatgac tttggcttcc tgggtgggca ataatttaga    900
tgatcctgca tccagagatc tagtagttaa ttatgtcaat actaacatgg gcctaaaact    960
```

<210> SEQ ID NO 29
<211> LENGTH: 960
<212> TYPE: DNA
<213> ORGANISM: Hepatitis B virus

<400> SEQUENCE: 29

```
cgcatgcgtg aacctttgc agctccactg ccgatccata ctgcggaact gctagctgcc     60
tgttttgctc gcagccggtc tggagcaaaa cttatcggga ctgataattc tgtcgtcctt    120
tcacggaaat atacatcatt tccatggctg ctaggctgtg ctgccaactg gatcatgcgc    180
gggacgtcct ttgtctacgt cccgtcggcg ctgaatcctg cggacgaccc ctctcggggc    240
cgtttgggga tctaccgtcc ccttctccgt ctgccgtacc ggccgtccac ggggcgcacc    300
tctctttacg cggactcccc gtgtgtgcct tctcatctgc cggaccgtgt gcacttcgct    360
tcacctctgc acgtcgcatg gagaccaccg tgaacgccca cctggtattg cccaaggtat    420
tgcataagag gactcttgga ctctcggcaa tgtcaacgac cgaccttgag gcatacttca    480
aagactgtgt gtttaaagac tgggaggagc tgggggagga gattaggcta aaggtctttg    540
tactaggagg ctgtaggcat aaattggtct gttcaccagc accatgcaac ttttcaccct    600
ctgcctaatc atctcatgtt catgtcctac tgttcaagcc tccaagctgt gccttgggtg    660
gctttggggc atggacattg acccttataa agaatttgga gcttctgtgg agttactctc    720
ttttttgcct tctgatttct ctccgtctgt tcgagatcta ctcgacaccg cctcagctct    780
ctaccgggag gccttagagt ctccggaaca ttgttcacct caccatacag cacttaggca    840
agctgtcctg tgttggggtg agttgatgac tctagctacc tgggtgggaa gtaatttgga    900
cgaccctgga tccagggatt tagtagtcac ctatgtcaat gttaatatgg gcctaaagtt    960
```

<210> SEQ ID NO 30
<211> LENGTH: 960
<212> TYPE: DNA
<213> ORGANISM: Hepatitis B virus

<400> SEQUENCE: 30

```
cgcatgcgtg aacctttgt ggctcctctg ccgatccata cggcggaact gctagctgcc     60
tgttttgctc gcagcaggtc tggggcaaat cttatcggga ctgataattc tgtcgtcctt    120
tcgcggaaat atacatcatt tccatggctg ctaggctgtg ctgccaactg gatcctgcgc    180
gggacgtcct ttgtctacgt cccgtcggcg ctgaatcctg cggacgaccc ctctcggggc    240
cgcttgggga tctaccgtcc ccttcttcgc ctgccgttcc ggccgtccac ggggcgcacc    300
tctctttacg cggtctcccc gtctgtgcct tctcatctgc cggaccgtgt gcacttcgct    360
tcacctctgc acgtcgcatg gagaccaccg tgaacgacca cctgaccttg cccaaggtct    420
tgcataagag gactcttgga ctcccagcaa tgtcaacgac cgaccttgag gcatacttca    480
aagactgtgt gtttaaagac tgggaggagt tggggaggag gatcaggtta aagatttatg    540
tattaggagg ctgtaggcat aaattggtct gcgcaccagc accatgcaac ttttcaccct    600
ctgcctaatc atctcttgtt catgtcctac tgttcaagcc tccaagctgt gccttgggtg    660
```

```
gctttaggac atggacattg acccttataa agaatttgga gcttctttgg agttactctc    720
ttttttgcct tctgatttct ttccatctgt tcgagatctc ctcgacaccg cctcagcttt    780
gtatcgggag gccttagagt ctcctgaaca ttgtacacct caccatacag cactcaggca    840
agcggtaata tgttggggtg agttgatgac tctagctact tgggtgggaa gtaatttgga    900
agaccctgcc tccagggatt tagtagtcag ctatgtcaat ggtcatatgg gcctaaaatt    960
```

<210> SEQ ID NO 31
<211> LENGTH: 960
<212> TYPE: DNA
<213> ORGANISM: Hepatitis B virus

<400> SEQUENCE: 31

```
cgcatgcgtg gaacctttgt ggctcctctg ccgatccata ctgcggaact gctagctgcc     60
tgttttgctc gcagcaggtc tggagcaaac attataggga ctgataattc cgtcgtcctt    120
tcgcggaaat atacgtcctt tccatggctg ctaggctgtg ctgccaactg gatcctgcgc    180
gggacgtcct ttgtctacgt cccgtcggcg ctgaatcctg cggacgaccc ctctcggggc    240
cgcttgggga tctaccgtcc ccttcttcgt ctgccgttcc ggccgtccac ggggcgcacc    300
tctctttacg cggtctcccc gtctgtgcct tctcatctgc cggcccgtgt gcacttcgct    360
tcacctctgc acgtcgcatg gagaccaccg tgaacgccca cctgaccttg cccaaggtat    420
tgcataagag gactcttgga ctctcagcaa tgtcaacgac cgaccttgag gcatacttca    480
aagactgtgt gtttaaagac tgggaggagt tgggggagga gatcaggtta aaggtctttg    540
tattaggagg ctgtaggcat aaattggtct gttcaccagc accatgcaac ttttcacct    600 ctgcctaatc atctcatgtt catgtcctac tgttcaagcc tccaagttgt gccttgggtg    660
gctttggggc atggacattg acccttataa agaatttgga gcttctgtgg agttactctc    720
ttttttgcct tctgatttct ttccatctat tcgagatctc ctcgacaccg cctcagcttt    780
gtatcgggag gccttagagt ctcctgaaca ttgttcacct caccatacag cactcaggca    840
agctgttcta tgttggggtg agttgatgac tctagctacc tgggtgggaa gtaatttgga    900
agaccctgcc tccagggatt tagtagtcag ctatgtcaat gttaatatgg ggctaaaaat    960
```

<210> SEQ ID NO 32
<211> LENGTH: 960
<212> TYPE: DNA
<213> ORGANISM: Hepatitis B virus

<400> SEQUENCE: 32

```
cgcatgcgtg gaacctttgt ggctcctctg ccgatccata ctgcggaact cctagcagct     60
tgttttgctc gcagcaggtc tggggcaaac ctactcggga cagataattc tgtggtttta    120
tcacggaagt atacgtcctt cccatggctg ctaggctgtg ctgccaactg gatcctgcgc    180
gggacgtcct ttgtctacgt cccgtcggcg ctgaatcccg cggacgaccc gtctcggggc    240
aagttgggcc tctaccgtcc tcttctccgt ctgccgttcc gaccgaccac ggggcgcacc    300
tctctttacg cggtctcccc gtctgtacct tctcatctgc cggcccgtgt gcacttcgct    360
tcacctctgc acgttgcatg gagaccaccg tgaacgcccc ctggaatttg ccaagagtgt    420
tacataagcg gactcttgga ctttcggaca tgtcaacgtc cgcaattgag acatacttca    480
aggactgtgt atttaaagac tgggaggagt caggggagga gattaggtta atgatctttg    540
tattaggagg ctgtaggcat aaattggtct gttcaccagc accatgcaac ttttcacct    600
```

| | |
|---|---:|
| ctgcctaatc atctcttgtt catgtcctac tgttcaagcc tccaagctgt gccttgggtg | 660 |
| gctttagggc atggacattg acccttataa agaatttgga gcttctgtgg agttactctc | 720 |
| ttttttgcct tctgatttct ttccgtcaat cagagacctc ctcgacaccg cctcagctct | 780 |
| ataccgagaa gccttagagt ctccagaaca ttgctcacct caccatacag cacttaggca | 840 |
| agctgtgcta tgttggggtg agttgatgaa tctggctacc tgggtgggaa gtaatttgga | 900 |
| agacccagca tccagggaac ttgtagtcag ctatgttaac attaatatgg gcctaaaaat | 960 |

<210> SEQ ID NO 33
<211> LENGTH: 378
<212> TYPE: DNA
<213> ORGANISM: Homo sapiens

<400> SEQUENCE: 33

| | |
|---|---:|
| tatcacagat tcttttttt taaattaaag taacatttcc aatctactaa tgctaatact | 60 |
| gtttcgtatt tatagctgat ttgatggagt tggacatggc catggaacca gacagaaaag | 120 |
| cggctgttag tcactggcag caacagtctt acctggactc tggaatccat tctggtgcca | 180 |
| ctaccacagc tccttctctg agtggtaaag gcaatcctga ggaagaggat gtggatacct | 240 |
| cccaagtcct gtatgagtgg gaacaggat tttctcagtc cttcactcaa gaacaagtag | 300 |
| ctggtaagag tattattttt cattgcctta ctgaaagtca gaatgcagtt ttgagaacta | 360 |
| aaaagttagt gtataata | 378 |

<210> SEQ ID NO 34
<211> LENGTH: 673
<212> TYPE: DNA
<213> ORGANISM: Homo sapiens

<400> SEQUENCE: 34

| | |
|---|---:|
| gtcgcctgcg ctgctctccg catgtcgctg gttcccccg gccgccctca accccagccg | 60 |
| gacgccgacc ccggggaggc ccacctggcg gaaggagggg gcggcggggg gcggccgtgc | 120 |
| gtcccagggc acgcacacca ggcactgggc caccagcgcg cggaaagccg ccgggtcccc | 180 |
| gcgctgcacc agccgccagc cctgggggcc caggcgccgc acgaacgtgg ccagcggcag | 240 |
| cacctcgcgg tagtggctgc gcagcaggga gcgcacggct cggcagcggg gagcgcgcgg | 300 |
| catcgcgggg gtggccgggg ccagggcttc ccacgtgcgc agcaggacgc agcgctgcct | 360 |
| gaaactcgcg ccgcgaggag agggcgggc gcggaaagg aaggggaggg gctgggaggg | 420 |
| cccggagggg gctgggccgg ggacccggga ggggtcggga cggggcgggg tccgcgcgga | 480 |
| ggaggcggag ctggaaggtg aagggggcagg acgggtgccc gggtccccag tccctccgcc | 540 |
| acgtggggaag cgcggtcctg ggcgtctgtg cccgcgaatc cactgggagc ccggcctggc | 600 |
| cccgacagcg cagctgctcc gggcggaccc gggggtctgg gccgcgcttc cccgcccgcg | 660 |
| cgccgctcgc gct | 673 |

<210> SEQ ID NO 35
<211> LENGTH: 779
<212> TYPE: DNA
<213> ORGANISM: Homo sapiens

<400> SEQUENCE: 35

| | |
|---|---:|
| ggttccttct ctgcaggccc aggtgaccca gggttggaag tgtctcatgc tggatcccca | 60 |
| cttttcctct tgcagcagcc agactgcctt ccgggtcact gccatggagg agccgcagtc | 120 |
| agatcctagc gtcgagcccc ctctgagtca ggaaacattt tcagacctat ggaaactgtg | 180 |

| | |
|---|---|
| agtggatcca ttggaagggc aggcccacca ccccccacccc aaccccagcc ccctagcaga | 240 |
| gacctgtggg aagcgaaaat tccatgggac tgactttctg ctcttgtctt tcagacttcc | 300 |
| tgaaaacaac gttctggtaa ggacaagggt tgggctgggg acctggaggg ctggggacct | 360 |
| ggagggctgg ggggctgggg ggctgaggac ctggtcctct gactgctctt ttcacccatc | 420 |
| tacagtcccc cttgccgtcc caagcaatgg atgatttgat gctgtccccg gacgatattg | 480 |
| aacaatggtt cactgaagac ccaggtccag atgaagctcc cagaatgcca gaggctgctc | 540 |
| cccccgtggc ccctgcacca gcagctccta caccggcggc ccctgcacca gcccctcct | 600 |
| ggccctgtc atcttctgtc ccttcccaga aaacctacca gggcagctac ggtttccgtc | 660 |
| tgggcttctt gcattctggg acagccaagt ctgtgacttg cacggtcagt tgccctgagg | 720 |
| ggctggcttc catgagactt caatgcctgg ccgtatcccc ctgcatttct tttgtttgg | 779 |

<210> SEQ ID NO 36
<211> LENGTH: 528
<212> TYPE: DNA
<213> ORGANISM: Homo sapiens
<400> SEQUENCE: 36

| | |
|---|---|
| gctgccgtct tccagttgct ttatctgttc acttgtgccc tgactttcaa ctctgtctcc | 60 |
| ttcctcttcc tacagtactc ccctgccctc aacaagatgt tttgccaact ggccaagacc | 120 |
| tgccctgtgc agctgtgggt tgattccaca cccccgcccg gcacccgcgt ccgcgccatg | 180 |
| gccatctaca gcagtcaca gcacatgacg gaggttgtga ggcgctgccc ccaccatgag | 240 |
| cgctgctcag atagcgatgg tgagcagctg gggctggaga gacgacaggg ctggttgccc | 300 |
| agggtcccca ggcctctgat tcctcactga ttgctcttag gtctggcccc tcctcagcat | 360 |
| cttatccgag tggaaggaaa tttgcgtgtg gagtatttgg atgacagaaa cacttttcga | 420 |
| catagtgtgg tggtgcccta tgagccgcct gaggtctggt ttgcaactgg ggtctctggg | 480 |
| aggaggggtt aagggtggtt gtcagtggcc ctccaggtga gcagtagg | 528 |

<210> SEQ ID NO 37
<211> LENGTH: 260
<212> TYPE: DNA
<213> ORGANISM: Homo sapiens
<400> SEQUENCE: 37

| | |
|---|---|
| aaaaaggcct cccctgcttg ccacaggtct ccccaaggcg cactggcctc atcttgggcc | 60 |
| tgtgttatct cctaggttgg ctctgactgt accaccatcc actacaacta catgtgtaac | 120 |
| agttcctgca tgggcggcat gaaccggagg cccatcctca ccatcatcac actggaagac | 180 |
| tccaggtcag gagccacttg ccaccctgca cactggcctg ctgtgcccca gcctctgctt | 240 |
| gcctctgacc cctgggccca | 260 |

<210> SEQ ID NO 38
<211> LENGTH: 436
<212> TYPE: DNA
<213> ORGANISM: Homo sapiens
<400> SEQUENCE: 38

| | |
|---|---|
| cctggttttt taaatgggac aggtaggacc tgatttcctt actgcctctt gcttctcttt | 60 |
| tcctatcctg agtagtggta atctactggg acgaacagc tttgaggtgc gtgtttgtgc | 120 |
| ctgtcctggg agagaccggc gcacagagga agagaatctc cgcaagaaag gggagcctca | 180 |

```
ccacgagctg cccccaggga gcactaagcg agcctggttt tttaaatggg acaggtagga    240
cctgatttcc ttactgcctc ttgcttctct tttcctatcc tgagtagcac tgcccaacaa    300
caccagctcc tctccccagc caaagaagaa accactggat ggagaatatt tcacccttca    360
ggtactaagt cttgggacct cttatcaagt ggaaagtttc cagtctaaca ctcaaaatgc    420
cgttttcttc ttgact                                                    436

<210> SEQ ID NO 39
<211> LENGTH: 453
<212> TYPE: DNA
<213> ORGANISM: Homo sapiens

<400> SEQUENCE: 39
cctggttttt taaatgggac aggtaggacc tgatttcctt actgcctctt gcttctcttt     60
tcctatcctg agtagtggta atctactggg acgaacagc tttgaggtgc gtgtttgtgc    120
ctgtcctggg agagaccggc gcacagagga agagaatctc cgcaagaaag gggagcctca    180
ccacgagctg cccccaggga gcactaagcg aggtaagcaa gcaggacaag aagcggtgga    240
ggagaccaag ggtgcagtta tgcctcagat tcacttttat cacctttcct tgcctctttc    300
ctagcactgc caacaacac cagctcctct ccccagccaa agaagaaacc actggatgga    360
gaatatttca cccttcaggt actaagtctt gggacctctt atcaagtgga agtttccag    420 tctaacactc aaaatgccgt tttcttcttg act                                 453

<210> SEQ ID NO 40
<211> LENGTH: 257
<212> TYPE: DNA
<213> ORGANISM: Homo sapiens

<400> SEQUENCE: 40
caattgtaac ttgaaccatc ttttaactca ggtactgtgt atatacttac ttctccccct     60
cctctgttgc tgcagatccg tgggcgtgag cgcttcgaga tgttccgaga gctgaatgag    120
gccttggaac tcaaggatgc ccaggctggg aaggagccag gggggagcag ggctcactcc    180
aggtgagtga cctcagcccc ttcctggccc tactcccctg ccttcctagg ttggaaagcc    240
ataggattcc attctca                                                   257

<210> SEQ ID NO 41
<211> LENGTH: 232
<212> TYPE: DNA
<213> ORGANISM: Homo sapiens

<400> SEQUENCE: 41
ttggtcaggg aaaaggggca cagaccctct cactcatgtg atgtcatctc tcctccctgc     60
ttctgtctcc tacagccacc tgaagtccaa aaagggtcag tctacctccc gccataaaaa    120
actcatgttc aagacagaag ggcctgactc agactgacat tctccacttc ttgttcccca    180
ctgacagcct cccaccccca tctctccctc ccctgccatt tgggttttg gg             232

<210> SEQ ID NO 42
<211> LENGTH: 120
<212> TYPE: DNA
<213> ORGANISM: Lambda phage

<400> SEQUENCE: 42
ctggtgccgc cgcaatggcc attaaccgcg ttgcttcatc cgcgatatcg cagtcggcgt     60
cacaggttgc ccgtgagaca aaggtacgcc ggaaactggt aaaggaaagg ccaggctga    120
```

<210> SEQ ID NO 43
<211> LENGTH: 120
<212> TYPE: DNA
<213> ORGANISM: Lambda phage

<400> SEQUENCE: 43
acgtgtcggc ggagcagatt gcgtatgttg ctcagttgca gcgttccggc gatgaagccg      60
gggcattgca ggcggcgaac gaggccgcaa cgaaagggtt tgatgaccag acccgccgcc     120

<210> SEQ ID NO 44
<211> LENGTH: 120
<212> TYPE: DNA
<213> ORGANISM: Lambda phage

<400> SEQUENCE: 44
gccgtggtgg ctggtctgcc gggggacgat tcataagttc cgctgtgtgc cgcatctcac      60
cgggcggcgc tttgagcacg gtgtgacgga ctgttacaca ctgttccggg atgcttatca     120

<210> SEQ ID NO 45
<211> LENGTH: 120
<212> TYPE: DNA
<213> ORGANISM: Lambda phage

<400> SEQUENCE: 45
catgtaccgg gcgatgttat tgaaatctgc gatgatgact atgccggtat cagcaccggt      60
ggtcgtgtgc tggcggtgaa cagccagacc cggacgctga cgctcgaccg tgaaatcacg     120

<210> SEQ ID NO 46
<211> LENGTH: 240
<212> TYPE: DNA
<213> ORGANISM: Lambda phage

<400> SEQUENCE: 46
ctggtgccgc cgcaatggcc attaaccgcg ttgcttcatc cgcgatatcg cagtcggcgt      60
cacaggttgc ccgtgagaca aaggtacgcc ggaaactggt aaaggaaagg gccaggctga     120
aaagggccac ggtcaaaaat ccgcaggcca gaatcaaagt taaccggggg gatttgcccg     180
taatcaagct gggtaatgcg cgggttgtcc tttcgcgccg caggcgtcgt aaaaagggc     240

<210> SEQ ID NO 47
<211> LENGTH: 240
<212> TYPE: DNA
<213> ORGANISM: Lambda phage

<400> SEQUENCE: 47
catgtaccgg gcgatgttat tgaaatctgc gatgatgact atgccggtat cagcaccggt      60
ggtcgtgtgc tggcggtgaa cagccagacc cggacgctga cgctcgaccg tgaaatcacg     120
ctgccatcct ccggtaccgc gctgataagc ctggttgacg gaagtggcaa tccggtcagc     180
gtggaggttc agtccgtcac cgacggcgtg aaggtaaaag tgagccgtgt tcctgacggt     240

<210> SEQ ID NO 48
<211> LENGTH: 180
<212> TYPE: DNA
<213> ORGANISM: Lambda phage

<400> SEQUENCE: 48
acgtgtcggc ggagcagatt gcgtatgttg ctcagttgca gcgttccggc gatgaagccg      60

```
gggcattgca ggcggcgaac gaggccgcaa cgaaagggtt tgatgaccag acccgccgcc    120
tgaaagagaa catgggcacg ctggagacct gggcagacag gactgcgcgg gcattcaaat    180

<210> SEQ ID NO 49
<211> LENGTH: 180
<212> TYPE: DNA
<213> ORGANISM: Lambda phage

<400> SEQUENCE: 49
gccgtggtgg ctggtctgcc gggggacgat tcataagttc cgctgtgtgc cgcatctcac    60
cgggcggcgc tttgagcacg gtgtgacgga ctgttacaca ctgttccggg atgcttatca   120
tctggcgggg attgagatgc cggactttca tcgtgaggat gactggtggc gtaacggcca   180

<210> SEQ ID NO 50
<211> LENGTH: 120
<212> TYPE: DNA
<213> ORGANISM: Lambda phage

<400> SEQUENCE: 50
agttatacat tctgccatag attatagcta aggcatgtaa taattcgtaa tcttttagcg    60
tattagcgac ccatcgtctt tctgatttaa taatagatga ttcagttaaa tatgaaggta   120

<210> SEQ ID NO 51
<211> LENGTH: 120
<212> TYPE: DNA
<213> ORGANISM: Lambda phage

<400> SEQUENCE: 51
cacacaacac catatgcatt taagtcgctt gaaattgcta taagcagagc atgttgcgcc    60
agcatgatta atacagcatt taatacagag ccgtgtttat tgagtcggta ttcagagtct   120

<210> SEQ ID NO 52
<211> LENGTH: 120
<212> TYPE: DNA
<213> ORGANISM: Lambda phage

<400> SEQUENCE: 52
gctgacagcc tgattgcaaa attcaaagaa gcgggcggaa cggtcagaga gattgatgta    60
tgagcagagt caccgcgatt atctccgctc tggttatctg catcatcgtc tgcctgtcat   120

<210> SEQ ID NO 53
<211> LENGTH: 120
<212> TYPE: DNA
<213> ORGANISM: Lambda phage

<400> SEQUENCE: 53
agaaacgaat gctgcagcgt cacaacaatc agccgccacg tctgcctcca ccgcggccac    60
gaaagcgtca gaggccgcca cttcagcacg agatgcggtg gcctcaaaag aggcagcaaa   120

<210> SEQ ID NO 54
<211> LENGTH: 120
<212> TYPE: DNA
<213> ORGANISM: Lambda phage

<400> SEQUENCE: 54
atcgccgtgc tgccggtgtc cggcacgctg gtcagccgga cgcgggcgct gcagccgtac    60
tcggggatga ccggttacaa cggcattatc gcccgtctgc aacaggctgc cagcgatccg   120
```

```
<210> SEQ ID NO 55
<211> LENGTH: 240
<212> TYPE: DNA
<213> ORGANISM: Homo sapiens

<400> SEQUENCE: 55
gaaaagagct aggaaggaca ggcaacttgg caaatcaaag ccctgggact aggggggttaa      60 aatacagctt cccctcttcc cacccgcccc agtctctgtc cctttttgtag gagggactta     120 gagaaggggt gggcttgccc tgtccagtta atttctgacc tttactcctg ccctttgagt     180
ttgatgatgc tgagtgtaca agcgttttct ccctaaaggg tgcagctgag ctaggcagca     240

<210> SEQ ID NO 56
<211> LENGTH: 240
<212> TYPE: DNA
<213> ORGANISM: Homo sapiens

<400> SEQUENCE: 56
gattacgaga ggtccctgag tcgcctgacg ctggacgaca tcgaacggtt ggccagccgc      60
ttcctgcacc ctgaagtgac tgagacaatg gagaagggct tctccaaata gaattctcgg     120
agcatgggga ggtgcccaac gccaggctac cgctgcatgt cgcactaagt gtgttctcct     180
gttgcagttg ggctcatcat cgtcatagct ggcatgtacc tggctctggc caggtgctag     240
```

PROBE COMBINATION FOR DETECTION OF CANCER

CROSS-REFERENCE TO RELATED APPLICATION

The present disclosure claims priority to U.S. provisional patent application No. 62/456,087, filed on Feb. 7, 2017, the entirety of which are incorporated herein by reference.

FIELD OF THE INVENTION

The present disclosure relates to a probe combination, and more particularly, to a combination of sequence-specific probes for detection of cancer.

BACKGROUND OF THE INVENTION

Hepadnaviridae is a family of viruses that has been reported to associate with pathogenesis of hepatitis, hepatocellular carcinoma (HCC) and cirrhosis. Hepatitis B virus (HBV) is among the most common members of the hepadnavirus family and is a small DNA virus that can be classified into genotypes A to J. While most adults infected with HBV can recover, about 5-10% of HBV infected patients are unable to clear the virus and become chronically infected. Those with chronic HBV infection are at high risk of developing HCC as HBV is capable of integrating into host genome and causing genetic and epigenetic alterations in hepatocytes.

A few methods for detection of HBV integration have been reported. For example, Jiang in "The effects of hepatitis B virus integration into the genomes of hepatocellular carcinoma patients" (*Genome Res.* (2012) 22, 593-601) and Sung in "Genome-wide survey of recurrent HBV integration in hepatocellular carcinoma" (*Nature Genetics* (2012) 44, 765-769) disclosed to utilize whole genome sequencing to detect HBV integration in HCC liver samples. However, efficiency of these direct sequencing methods was poor. As reported by Jiang, as much as 25-35 million 75-bp reads on average were generated for each data set, and the typical numbers of HBV and junctions reads for Jiang's data sets were 6 million and only 400 reads, respectively. Further, there has yet been any direct sequencing based studies that can detect HBV integration from circulating tumor DNA (ctDNA) samples.

Later on, Li in "HIVID: An efficient method to detect HBV integration using low coverage sequencing" (*Genomics* (2013) 102:4, 338-344)" and Zhao in "Genomic and oncogenic preference of HBV integration in hepatocellular carcinoma" (*Nature Communications* (2016) 7:12992) disclosed the use of sequence-capture probes designed according to sequences the HBV genome for detection of HBV integration. However, neither Li nor Zhao provided a clear idea regarding the design rationale of their probes. Furthermore, efficiency of the probes reported by Li and Zhao was poor. In both Li and Zhao, the average human ratio was as high as 83.7% and the average HBV alignment ratio and average integration rate were as low as 0.08% and 0.01% respectively, suggesting that the probes were still inefficient and ineffective in detecting HBV integration.

BRIEF SUMMARY OF THE INVENTION

The present invention provides a panel of probe combinations and the analytic methodology to be used therewith that are highly sensitive and efficient in capture viral DNA and viral-host junctions.

An embodiment of the present invention provides a probe combination for detecting cancer. The probe combination includes one or more sets of partial hepatitis B virus (HBV) targeting probes. When sequences of each of the sets of partial HBV targeting probes are aligned, an overall sequence of the aligned partial HBV targeting probes matches a reference sequence of a direct repeat (DR) region of a genome of a HBV genotype. In the aligned set of partial HBV targeting probes, each of the partial HBV targeting probes overlap with one or two adjacent partial HBV targeting probes by a portion of a length of the partial HBV targeting probes.

In a preferred embodiment, the HBV genotype includes genotype A, genotype B, genotype C, genotype D, genotype E, genotype F, genotype G, genotype H, genotype I and genotype J.

In a preferred embodiment, the reference sequence of the DR region includes SEQ ID NOs. 3-32.

In a preferred embodiment, the probe combination includes or further includes one or more sets of full HBV targeting probes. When sequences of each of the sets of full HBV targeting probes are aligned, an overall sequence of the aligned full HBV targeting probes matches a reference sequence of the genome of the HBV genotype. In the aligned set of full HBV targeting probes, each of the full HBV targeting probes overlap with one or two adjacent full HBV targeting probes by a portion of a length of one of the full HBV targeting probes.

In a preferred embodiment, the probe combination further includes one or more sets of hotspot gene targeting probes. When sequences of the each of the sets of hotspot gene targeting probes are aligned, an overall sequence of the aligned hotspot gene targeting probes matches a reference sequence of a cancer hotspot gene. In the aligned set of hotspot gene targeting probes, each of the hotspot gene targeting probes overlap with one or two adjacent hotspot gene targeting probes by a portion of a length of the hotspot gene targeting probes.

In a preferred embodiment, the cancer hotspot gene includes CTNNB1, TERT, and TP53 genes.

In a preferred embodiment, the reference sequence of the cancer hotspot gene comprises SEQ ID NOs. 33-41.

In a preferred embodiment, the probe combination further includes one or more sets of exogenous gene targeting probes. When sequences of the exogenous gene targeting probes are aligned, an overall sequence of the aligned set of exogenous gene targeting probes matches a reference sequence of an exogenous gene. In the aligned set of exogenous gene targeting probes, each of the exogenous gene targeting probes overlap with one or two adjacent exogenous gene targeting probes by a portion of a length of the exogenous gene targeting probes.

In a preferred embodiment, the exogenous gene originates a lambda phage.

In a preferred embodiment, the reference sequence of the exogenous gene comprises SEQ ID NOs. 42-54.

In a preferred embodiment, the probe combination further includes one or more sets of endogenous gene targeting probes. When sequences of the endogenous gene targeting probes are aligned, a sequence of the aligned set of endogenous gene targeting probes matches a reference sequence of an endogenous gene. In the aligned set of endogenous gene targeting probes, each of the endogenous gene targeting probes overlap with one or two adjacent endogenous gene targeting probes by a portion of a length of the endogenous gene targeting probes.

In a preferred embodiment, the endogenous gene includes GAPDH and GdX genes.

In a preferred embodiment, the reference sequence of the endogenous gene comprises SEQ ID NO. 55 and SEQ ID NO. 56.

Preferably, the cancer detected by the probe combination of the various embodiment includes hepatocellular carcinoma.

Preferably, the probe combination of the various embodiments is used for capturing target nucleotide fragments having viral-host junctions from DNA obtained for a specimen of a subject infected with HBV.

Preferably, the DNA obtained from the specimen includes genomic DNA and circulating tumor DNA (ctDNA) of the subject.

Preferably, the specimen comprises biological fluid and liver tissues.

In sum, the present invention according to the aforementioned embodiments provides a powerful and versatile tool for detection of viral infection and viral infection induced cancer. The embodiments of the present invention can be applied to detect presence of various types of DNA viruses and viral integration. The probe combination designed according to the embodiments ensures optimal viral/host sequence coverage and considers genetic stability, and is thus demonstrated to be highly sensitive, efficient, and reliable.

BRIEF DESCRIPTION OF THE DRAWINGS

The accompanying drawings illustrate one or more embodiments of the present invention and, together with the written description, explain the principles of the present invention. Wherever possible, the same reference numbers are used throughout the drawings to refer to the same or like elements of an embodiment.

FIG. 7 is an experimental result showing the NGS statistics of DNA samples hybridized by a probe combination in accordance with an embodiment of the present invention.

In accordance with common practice, the various described features are not drawn to scale and are drawn to emphasize features relevant to the present disclosure. Like reference characters denote like elements throughout the figures and text.

DETAILED DESCRIPTION OF THE PREFERRED EMBODIMENTS

Figure 1:
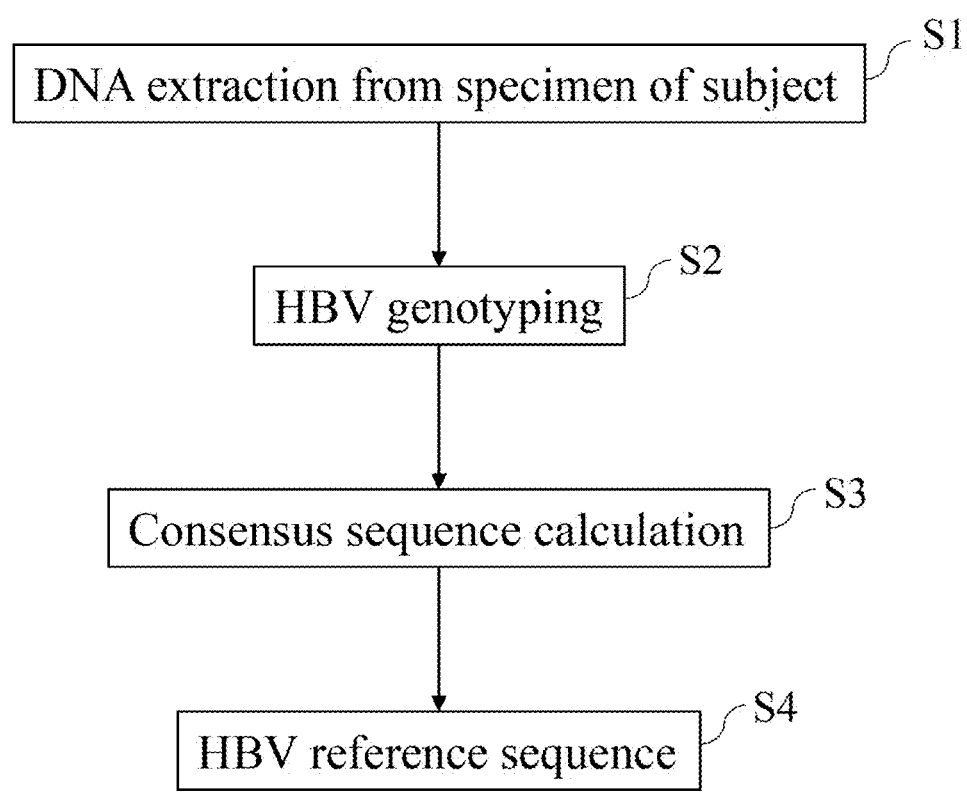
FIG. 1 is a flowchart depicting the steps of obtaining a reference sequence in accordance with an embodiment of the present invention.

The present invention will now be described more fully hereinafter with reference to the accompanying drawings illustrating various exemplary embodiments of the invention. The present invention may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the terms "and/or" and "at least one" include any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present disclosure.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

An aspect of the present invention provides a probe combination that includes one or more sets of sequence targeting probes. The probes may include single stranded oligonucleotides and polynucleotides, such as single stranded deoxyribonucleic acids (ssDNA), ribonucleic acids (RNA), and artificial nucleotides. The probe combination may be used for detection of viral infection or viral infection induced cancer, especially those caused by or associated with DNA virus. In some embodiments, the probe combination may be used for detecting infection with hepatitis B virus (HBV), human papillomavirus (HPV), Epstein-Barr virus (EBV), herpes virus 8 (HHV-8), human T-lymphotropic virus (HTLV), Merkel cell polyomavirus (MCV), or other DNA virus. In other embodiments, the probe combination may be used for detection for hepatocellular carcinoma, liver cancer, cervical cancer, penile cancer, anal cancer, vaginal cancer, vulvar cancer, oral cancer, oropharyngeal cancer, nasopharyngeal cancer, head and neck cancer, lymphoma, primary effusion lymphoma, stomach cancer, Kaposi sarcoma, Merkel cell carcinoma, or other cancer associated with infection with the DNA viruses.

According to an embodiment of the present invention, the probe combination includes one or more sets of full viral sequence targeting probes. When sequences of each of the sets of full viral sequence targeting probes are aligned, an overall sequence of the aligned set of full viral sequence targeting probes matches a reference sequence of a genome of a genotype of a target virus. The target virus may include various genotypes of the aforementioned DNA viruses. For example, in cases where HBV is the target virus, the genotype thereof may include genotype A, genotype B, genotype C, genotype D, genotype E, genotype F, genotype G, genotype H, genotype I and genotype J. The reference sequence of the viral genome may be retrieved from the NCBI GenBank or calculated from sequences obtained from clinical specimens. For example, reference sequences for HBV genotype A may be retrieved from NCBI GenBank (https://www.ncbi.nlm.nih.gov/genbank/) Accession No. AP007263, HE974383 or HE974381; reference sequences for HBV genotype B may be retrieved from GenBank Accession No. AB981581, AB602818, or AB554017; reference sequences for HBV genotype C may be retrieved from GenBank Accession No. LC360507, AB644287 or AB113879; reference sequences for HBV genotype D may be retrieved from GenBank Accession No. HE815465, HE974382 or AB554024; reference sequences for HBV genotype E may be retrieved from GenBank Accession No. HE974380, HE974384, AP007262; reference sequences for HBV genotype F may be retrieved from GenBank Accession No. DQ823095, AB036909 or AB036920; reference sequences for HBV genotype G may be retrieved from GenBank Accession No. AB625342, HE981176 or GU563559; reference sequences for HBV genotype H may be retrieved from GenBank Accession No. AB298362, AB846650, AB516395; reference sequences for HBV genotype I may be retrieved from GenBank Accession No. EU833891, KF214680 or KU950741; and reference sequences for HBV genotype J may be retrieved from GenBank Accession No. AB486012.

In an exemplary embodiment, the probe combination includes two sets of full HBV targeting probes. When sequences of one set of the full HBV targeting probes are aligned, an overall sequence of the aligned full HBV targeting probes matches a reference sequence of a genome of HBV genotype B (SEQ ID NO. 1). Likewise, when sequences of the other sets of the full HBV targeting probes are aligned, an overall sequence of the aligned full HBV targeting probes matches a reference sequence of a genome of HBV genotype C (SEQ ID NO. 2). In the exemplary embodiment, the reference sequence of the HBV genome is obtained as shown in FIG. 1. As in Step S1, DNA were extracted from specimens, such as biological fluid (e.g., blood, lymph, urine, sweat, saliva, tears, or intestinal fluid) and tissues (e.g., liver tissues), of patients with chronic HBV infection. The extracted DNA contains genomic DNA (gDNA) and/or circulating tumor DNA (ctDNA) of the patients. As in Step S2, the extracted DNA are sequenced and classified according to known sequences of various HBV genotypes as retrieved from the NCBI GenBank. In the exemplary embodiment, HBV genotype B and HBV genotype C were chosen for their prevalence among hepatocellular carcinoma (HCC) patients in Taiwan; however, embodiments of the present invention are not limited only to genotypes B and C of HBV, but encompass various genotypes of all DNA viruses that can cause persistent infection. As in Step S3, sequence of each of the chosen genotypes was aligned and calculated by the Clustal algorithm to obtain a consensus sequence of the virus genotype according to the major allele (i.e., the most common nucleotide) at each position of the sequence. Finally, the consensus sequence is used as a reference sequence for the virus genotype. In the exemplary embodiment, the reference sequences of the HBV genome include consensus sequences of HBV genotype B and genotype C, each covering all of the 3191 base pairs (bp) of the HBV genotype B or C genome.

Figure 2A:
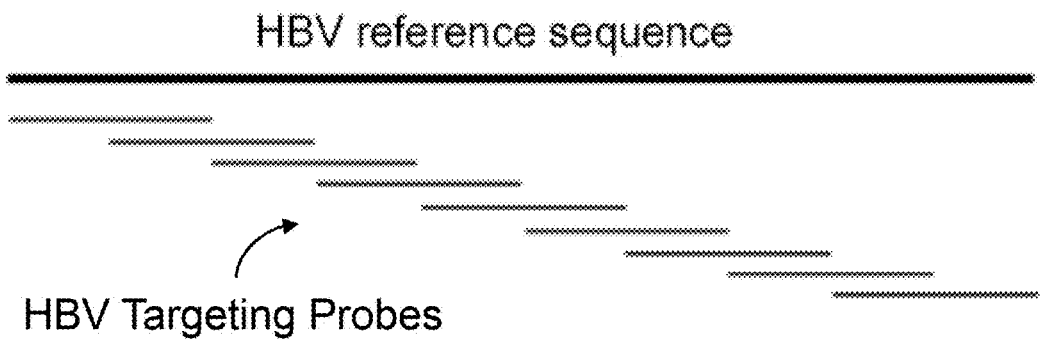
FIGS. 2A and 2B are schematic illustrations showing the design concept of the probes in accordance with an embodiment of the present invention.
Figure 2B:
Figure 2B:

In the embodiment, the viral sequence targeting probes are so designed that when sequences of the full viral sequence targeting probes are aligned, each of the full viral sequence targeting probes overlap with the immediately adjacent full viral sequence targeting probes by a portion of the length of the full viral sequence targeting probe. In the exemplary embodiment as illustrated in FIG. 2A, each of the full HBV targeting probes overlap with one or two immediately adjacent full HBV targeting probes by a portion of the length of the full HBV targeting probe. The portion of sequence overlapping may vary and is preferably 50% (denoted 2× tiling density) or 75% (denoted 4× tiling density), as illustrated in FIG. 2B. In an exemplary embodiment in which the probes are designed to extend 120 bp in length with a 2× tiling density, each of the probes would overlap with the immediate adjacent probe for 60 bp. Likewise, if the probes are 120 bp in length with a 4× tiling density, each of the probes would overlap with the immediate adjacent probe for 90 bp.

Furthermore, structure of the viral genome may also be taken into consideration when designing the probes. In the exemplary embodiment, considering the HBV genome is circular in nature, the last probe of the full HBV targeting probes that extends beyond the terminal 3191 position of the reference sequence of the HBV genome is designed to continue at the start (i.e., position 1) of the reference sequence. For example, a probe having a length of 120 bp and starting at position 3121 of the reference sequence of the HBV genome would consist of a 71-bp region corresponding to positions 3121-3191, followed by a 49-bp region corresponding to positions 1-49.

It is to be understood that the embodiments of the present invention do not limit the lengths of the probes; the lengths of the probes may be designed according to cost, capture efficiency, sensitivity, specificity, or other specific concerns. In some embodiments, the possible number or amount N of the probes for any given reference sequence may be calculated according to Equation (1).

$$N = \sum_{p=min}^{max} L - P + 1 \qquad (1)$$

In Equation 1, L represents the length of the reference sequence, and P represents the length of the probes, which may range from a minimum length (denoted mi) to a maximum length (denoted max). For example, a total of 220,597 probes, ranging from 50 bp to 120 bp, can be designed for the 3191-bp-long reference sequence of the HBV genotype B or C genome.

According to an embodiment of the present invention, the probe combination includes one or more sets of partial viral sequence targeting probes. When sequences of the partial viral sequence targeting probes are aligned, an overall sequence of the aligned set of partial viral sequence targeting probes matches a reference sequence of a characteristic region on the genome of the target virus. In the aligned set of partial viral sequence targeting probes, each of the partial viral sequence targeting probes overlap with the immediately adjacent partial viral sequence targeting probes by a portion of the length of the partial viral sequence targeting probe. In some embodiments, the characteristic region may include a region between direct repeat 1 (DR1) and direct repeat 2 (DR2) on the HBV genome. In other embodiments, the characteristic region may be the region between DR1 and DR2 plus two elongated regions extending from two ends of the region to reach a predetermined length. For example, in defining a 960-bp-long reference sequence for a direct repeat (DR) region, assuming that DR1 and DR2 are located at positions 360-370 and 594-604 on a viral genome, the reference sequence of the DR region may be defined as the region between DR1 and DR2 with further elongation of 360 bp from two ends of the region. Consequently, reference sequence for a DR region on the HBV genotype A genome may be SEQ ID NOs. 3-5; reference sequence for a DR region on the HBV genotype B genome may be SEQ ID NOs. 6-9; reference sequence for a DR region on the HBV genotype C genome may be SEQ ID NOs. 10-13; reference sequence for a DR region on the HBV genotype D genome may be SEQ ID NOs. 14-16; reference sequence for a DR region on the HBV genotype E genome may be SEQ ID NOs. 17-19; reference sequence for a DR region on the HBV genotype F genome may be SEQ ID Nos. 20-22; reference sequence for a DR region on the HBV genotype G genome may be SEQ ID NOs. 23-25; reference sequence for a DR region on the HBV genotype H genome may be SEQ ID NOs. 26-28; reference sequence for a DR region on the HBV genotype genome I may be SEQ ID NOs. 29-31; and reference sequence for a DR region on the HBV genotype J genome may be SEQ ID NO. 32.

In an exemplary embodiment, the probe combination may include two sets of partial HBV targeting probes. When sequences of one set of the partial HBV targeting probes are aligned, an overall sequence of the aligned partial HBV targeting probes matches a reference sequence of the direct repeat (DR) region of the genome of HBV genotype B (SEQ ID NO. 9) or the DR region of the HBV genotype C genome (SEQ ID NO. 13). The DR region may be defined as positions 1190-2234, positions 1231-2190 or other characteristic range on the HBV genome. Similar to the aforementioned, each of the partial HBV targeting probes overlap with one or two immediately adjacent partial HBV targeting probes by a portion of the length of the partial HBV targeting probe. The portion of sequence overlapping may be, but is not limited to, 50% (i.e., 2× tiling density) or 75% (i.e., 4× tiling density).

The possible number of the partial HBV targeting probes for the reference sequence of the DR region (SEQ ID NOs. 9, 13) may be calculated according to the aforementioned Equation (1). For example, a total of 62,196 probes, ranging from 50 bp to 120 bp, can be designed for the 960-bp-long reference sequence of the DR region of the HBV genome.

According to an embodiment of the present invention, the probe combination includes a set of the full viral sequence probes and a set of the partial viral sequence probes. The full and partial viral sequence probes are combined to enhance sequence coverage over the reference sequences of the viral genome. In the exemplary embodiment, the partial HBV targeting probes are designed to cover between the full HBV targeting probes at the DR region. For example, assuming that the full HBV targeting probes are 120 bp in length and start at positions 1, 61, and 121 (2× tiling density), the partial HBV targeting probes having 2× tiling would start at 31, 91, and 151. In other words, the DR region would be covered by two sets of probes (i.e., the full HBV targeting probes and the partial HBV targeting probes) with a 4× tiling density (i.e., each chain overlaps with 75% of its immediate adjacent chain).

According to an embodiment of the present invention, the probe combination further includes one or more sets of hotspot gene targeting probes. When sequences of each of the set of hotspot gene targeting probes are aligned, an overall sequence of the aligned set of hotspot gene targeting probes matches a reference sequence of a cancer hotspot gene. In the aligned set of hotspot gene targeting probes, each of the hotspot gene targeting probes overlap with the immediately adjacent hotspot gene targeting probes by a portion of the length of the hotspot gene targeting probe. The portion of sequence overlapping may be, but is not limited to, 50% (i.e., 2× tiling density) or 75% (i.e., 4× tiling density).

The reference sequence of the cancer hotspot gene is retrievable from the NCBI gene database. The cancer hotspot gene may include, but is not limited to, at least one of the following genes, as identified by Entrez Gene IDs according to the NCBI gene database (www.ncbi.nlm.nih.gov/entrez/query.fcgi?db=gene): ABL1 (Entrez Gene ID: 25), ABL2 (Entrez Gene ID: 27), ACSL3 (Entrez Gene ID: 2181), AF15Q14 (Entrez Gene ID: 57082), AF1Q (Entrez Gene ID: 10962), AF3p21 (Entrez Gene ID: 51517), AF5q31 (Entrez Gene ID: 27125), AKAP9 (Entrez Gene ID: 10142), AKT1 (Entrez Gene ID: 207), AKT2 (Entrez Gene ID: 208), ALDH2 (Entrez Gene ID: 217), ALK (Entrez Gene ID: 238), ALO17 (Entrez Gene ID: 57674), APC (Entrez Gene ID: 11789), ARHGEF12 (Entrez Gene ID: 23365), ARHH (Entrez Gene ID: 399), ARIDIA (Entrez Gene ID: 8289), ARID2 (Entrez Gene ID: 196528), ARNT (Entrez Gene ID: 405), ASPSCR1 (Entrez Gene ID: 79058), ASXL1 (Entrez Gene ID: 171023), ATF1 (Entrez Gene ID: 466), ATIC (Entrez Gene ID: 471), ATM (Entrez Gene ID: 472), ATRX (Entrez Gene ID: 546), BAPI (Entrez Gene ID: 8314), BCL10 (Entrez Gene ID: 8915), BCL11A (Entrez Gene ID: 53335), BCL11B (Entrez Gene ID: 64919), BCL2 (Entrez Gene ID: 596), BCL3 (Entrez Gene ID: 602), BCLS (Entrez Gene ID: 603), BCL6 (Entrez Gene ID: 604), BCL7A (Entrez Gene ID: 605), BCL9 (Entrez Gene ID: 607), BCOR (Entrez Gene ID: 54880), BCR (Entrez Gene ID: 613), BHD (Entrez Gene ID: 50947), BIRC3 (Entrez Gene ID: 330), BLM (Entrez Gene ID: 641), BMPRIA (Entrez Gene ID: 12166), BRAF (Entrez Gene ID: 673), BRCA1 (Entrez Gene ID: 672), BRCA2 (Entrez Gene ID: 675), BRD3 (Entrez Gene ID: 8019), BRD4 (Entrez Gene ID: 23476), BRIP1 (Entrez Gene ID: 83990), BTG1 (Entrez Gene ID: 694), BUB1B (Entrez Gene ID: 701), C15orf55 (Entrez Gene ID: 144535), C16orf75 (Entrez Gene ID: 387882), CANT1 (Entrez Gene ID: 124583), CARD11 (Entrez Gene ID: 84433), CARs (Entrez Gene ID: 833), CBFB (Entrez Gene ID: 865), CBL (Entrez Gene ID: 867), CBLB (Entrez Gene ID: 868), CBLC (Entrez Gene ID: 23624), CCNB1IP1 (Entrez Gene ID: 57820), CCND1 (Entrez Gene ID: 595), CCND2 (Entrez Gene ID: 894), CCND3 (Entrez Gene ID: 896), CCNE1 (Entrez Gene ID: 898), CD273 (Entrez Gene ID: 80380), CD274 (Entrez Gene ID: 29126), CD74 (Entrez Gene ID: 972), CD79A (Entrez Gene ID: 973), CD79B (Entrez Gene ID: 974), CDH1 (Entrez Gene ID: 999), CDH11 (Entrez Gene ID: 1009), CDK12 (Entrez Gene ID: 51755), CDK4 (Entrez Gene ID: 1019), CDK6 (Entrez Gene ID: 1021), CDKN2A (Entrez Gene ID: 1029), CDKN2C (Entrez Gene ID: 1031), CDX2 (Entrez Gene ID: 1045), CEBPA (Entrez Gene ID: 1050), CEP1 (Entrez Gene ID: 11064), CHCHD7 (Entrez Gene ID: 79145), CHEK2 (Entrez Gene ID: 11200), CHIC2 (Entrez Gene ID: 26511), CHN 1 (Entrez Gene ID: 1123), CIC (Entrez Gene ID: 23152), CIITA (Entrez Gene ID: 4261), CLTC (Entrez Gene ID: 1213), CLTCL1 (Entrez Gene ID: 8218), CMKOR1 (Entrez Gene ID: 57007), CoL1A1 (Entrez Gene ID: 1277), CPBP (Entrez Gene ID: 1316), COX6C (Entrez Gene ID: 1345), CREB1 (Entrez Gene ID: 1385), CREB3L1 (Entrez Gene ID: 90993), CREB3L2 (Entrez Gene ID: 64764), CREBBP (Entrez Gene ID: 1387), CRLF2 (Entrez Gene ID: 64109), CRTC3 (Entrez Gene ID: 64784), CTNNB1 (catenin beta 1; Entrez Gene ID: 1499), CYLD (Entrez Gene ID: 1540), D10S170 (Entrez Gene ID: 8030), DAXX (Entrez Gene ID: 1616), DDB2 (Entrez Gene ID: 1643), DDX10 (Entrez Gene ID: 1662), DDXS (Entrez Gene ID: 1655), DDX6 (Entrez Gene ID: 1656), DEK (Entrez Gene ID: 7913), DICER1 (Entrez Gene ID: 23405). DNMT3A (Entrez Gene ID: 1788). DUX4 (Entrez Gene ID: 100288687). EBF1 (Entrez Gene ID: 1879), EGFR (Entrez Gene ID: 1956), EIF4A2 (Entrez Gene ID: 1974), ELF4 (Entrez Gene ID: 2000), ELK4 (Entrez Gene ID: 2005), ELKS (Entrez Gene ID: 23085), ELL (Entrez Gene ID: 8178), ELN (Entrez Gene ID: 2006), EML4 (Entrez Gene ID: 27436), EP300 (Entrez Gene ID: 2033), EPS 15 (Entrez Gene ID: 2060), ERBB2 (Entrez Gene ID: 2064), ERCC2 (Entrez Gene ID: 2068), ERCC3 (Entrez Gene ID: 2071), ERCC4 (Entrez Gene ID: 2072), ERCC5 (Entrez Gene ID: 2073), ERG (Entrez Gene ID: 2078), ETV1 (Entrez Gene ID: 2115), ETV4 (Entrez Gene ID: 2118), ETV5 (Entrez Gene ID: 2119), ETV6 (Entrez Gene ID: 2120), EVI1 (Entrez Gene ID: 2122), EWsR1 (Entrez Gene ID: 2130), EXT1 (Entrez Gene ID: 2131), EXT2 (Entrez Gene ID: 2132), EZH2 (Entrez Gene ID: 2146), FACL6 (Entrez Gene ID: 23305), FAM22A (Entrez Gene ID: 728118), FAM22B (Entrez Gene ID: 729262), FAM46C (Entrez Gene ID: 54855), FANCA (Entrez Gene ID: 2175), FANCC (Entrez Gene ID: 2176), FANCD2 (Entrez Gene ID: 2177), FANCE (Entrez Gene ID: 2178), FANCF (Entrez Gene ID: 2188), FANCG (Entrez Gene ID: 2189), FBXO11 (Entrez Gene ID: 80204), FBXW7 (Entrez Gene ID: 55294), FCGR2B (Entrez Gene ID: 2213), FEV (Entrez Gene ID: 54738), FGFR1 (Entrez Gene ID: 2260), FGFR1OP (Entrez Gene ID: 11116), FGFR2 (Entrez Gene ID: 2263), FGFR3 (Entrez Gene ID: 2261), FH (Entrez Gene ID: 2271), FHIT (Entrez Gene ID: 2272), FIPIL1 (Entrez Gene ID: 81608), FLII (Entrez Gene ID: 2313), FLT3 (Entrez Gene ID: 2322), FNBP1 (Entrez Gene ID: 23048), FOXL2 (Entrez Gene ID: 668), FOXO1 (Entrez Gene ID: 2308), FOXO3A (Entrez Gene ID: 2309), FOXP1 (Entrez Gene ID: 27086), FSTL3 (Entrez Gene ID: 10272), FUBP1 (Entrez Gene ID: 8880), FUS (Entrez Gene ID: 2521), FVT1 (Entrez Gene ID: 2531), GAS7 (Entrez Gene ID: 8522), GATA1 (Entrez Gene ID: 2623), GATA2 (Entrez Gene ID: 2624), GATA3 (Entrez Gene ID: 2625), GMPS (Entrez Gene ID: 8833), GNA11 (Entrez Gene ID: 2767), GNAQ (Entrez Gene ID: 2776), GNAS (Entrez Gene ID: 2778), GOLGA5 (Entrez Gene ID: 9950), GOPC (Entrez Gene ID: 57120), GPC3 (Entrez Gene ID: 2719), GPHN (Entrez Gene ID: 10243), GRAF (Entrez Gene ID: 23092), HCMOGT-1 (Entrez Gene ID: 92521), HEAB (Entrez Gene ID: 10978), HERPUD1 (Entrez Gene ID: 9709), HEY1 (Entrez Gene ID: 23462), HIP1 (Entrez Gene ID: 3092), HIST1H4I (Entrez Gene ID: 8294), HLF (Entrez Gene ID: 3131), HLXB9 (Entrez Gene ID: 3110), HMGA1 (Entrez Gene ID: 3159), HMGA2 (Entrez Gene ID: 8091), HNRNPA2B1 (Entrez Gene ID: 3181), HOOK3 (Entrez Gene ID: 84376), HOXA11 (Entrez Gene ID: 3207), HOXA13 (Entrez Gene ID: 3209), HOXA9 (Entrez Gene ID: 3205), HOXC11 (Entrez Gene ID: 3227), HOXC13 (Entrez Gene ID: 3229), HOXD11 (Entrez Gene ID: 3237), HOXD13 (Entrez Gene ID: 3239), HRAS (Entrez Gene ID: 3265), HRPT2 (Entrez Gene ID: 79577), HSPCA (Entrez Gene ID: 3320), HSPCB (Entrez Gene ID: 3326), IDH1 (Entrez Gene ID: 3417), IDH2 (Entrez Gene ID: 3418), IGH@ (Entrez Gene ID: 3492), IGK@ (Entrez Gene ID: 50802), IGL@ (Entrez Gene ID: 3535), IKZF1 (Entrez Gene ID: 10320), IL2 (Entrez Gene ID: 3558), IL21R (Entrez Gene ID: 50615), IL6ST (Entrez Gene ID: 3572), IL7R (Entrez Gene ID: 3575), IRF4 (Entrez Gene ID: 3662), IRTA1 (Entrez Gene ID: 83417), ITK (Entrez Gene ID: 3702), JAK1 (Entrez Gene ID: 3716), JAK2 (Entrez Gene ID: 3717), JAK3 (Entrez Gene ID: 3718), JAZF1 (Entrez Gene ID: 221895), JUN (Entrez Gene ID: 3725), KDR (Entrez Gene ID: 3791), KIAA1549 (Entrez Gene ID: 57670), KIT (Entrez Gene ID: 3815), KLK2 (Entrez Gene ID: 3817), KRAS (Entrez Gene ID: 3845), KTN1 (Entrez Gene ID: 3895), LAF4 (Entrez Gene ID: 3899), LASP1 (Entrez Gene ID: 3927), LCK (Entrez Gene ID: 3932), LCP1 (Entrez Gene ID: 3936), LCX (Entrez Gene ID: 80312), LHFP (Entrez Gene ID: 10186), LIFR (Entrez Gene ID: 3977), LMO1 (Entrez Gene ID: 4004), LMO2 (Entrez Gene ID: 4005), LPP (Entrez Gene ID: 4026), LYL1 (Entrez Gene ID: 4066), MADH4 (Entrez Gene ID: 4089), MAF (Entrez Gene ID: 4094), MAFB (Entrez Gene ID: 9935), MALT1 (Entrez Gene ID: 10892), MAML2 (Entrez Gene ID: 84441), MAP2K4 (Entrez Gene ID: 6416), MDM2 (Entrez Gene ID: 4193), MDM4 (Entrez Gene ID: 4194), MDS1 (Entrez Gene ID: 2122), MDS2 (Entrez Gene ID: 259283), MECT1 (Entrez Gene ID: 23373), MED12 (Entrez Gene ID: 9968), MEN1 (Entrez Gene ID: 4221), MET (Entrez Gene ID: 4233), MITF (Entrez Gene ID: 4286), MKL1 (Entrez Gene ID: 57591), MLF1 (Entrez Gene ID: 4291). MLH1 (Entrez Gene ID: 4292), MLL (Entrez Gene ID: 4297), MLL2 (Entrez Gene ID: 8085), MLL3 (Entrez Gene ID: 58508), MLLT1 (Entrez Gene ID: 4298), MLLT10 (Entrez Gene ID: 8028), MLLT2 (Entrez Gene ID: 4299), MLLT3 (Entrez Gene ID: 4300), MLLT4 (Entrez Gene ID: 4301), MLLT6 (Entrez Gene ID: 4302), MLLT7 (Entrez Gene ID: 4303), MN1 (Entrez Gene ID: 4330), MPL (Entrez Gene ID: 4352), MSF (Entrez Gene ID: 10801), MSH2 (Entrez Gene ID: 4436), MSH6 (Entrez Gene ID: 2956), MsI2 (Entrez Gene ID: 124540), MSN (Entrez Gene ID: 4478), MTCP1 (Entrez Gene ID: 4515), MUC 1 (Entrez Gene ID: 4582), MUTYH (Entrez Gene ID: 4595), MYB (Entrez Gene ID: 4602), MYC (Entrez Gene ID: 4609), MYCL1 (Entrez Gene ID: 4610), MYCN (Entrez Gene ID: 4613), MYD88 (Entrez Gene ID: 4615), MYH11 (Entrez Gene ID: 4629), MYH9 (Entrez Gene ID: 4627), MYST4 (Entrez Gene ID: 23522), NACA (Entrez Gene ID: 4666), NBS1 (Entrez Gene ID: 4683), NCOA1 (Entrez Gene ID: 8648), NCOA2 (Entrez Gene ID: 10499), NCOA4 (Entrez Gene ID: 8031), NDRG1 (Entrez Gene ID: 10397), NF1 (Entrez Gene ID: 4763), NF2 (Entrez Gene ID: 4771), NFE2L2 (Entrez Gene ID: 4780), NFIB (Entrez Gene ID: 4781), NFKB2 (Entrez Gene ID: 4791), NIN (Entrez Gene ID: 51199), NKX2-1 (Entrez Gene ID: 7080), NONO (Entrez Gene ID: 4841), NOTCH1 (Entrez Gene ID: 4851), NOTCH2 (Entrez Gene ID: 4853), NPM1 (Entrez Gene ID: 4869), NR4A3 (Entrez Gene ID: 8013), NRAS (Entrez Gene ID: 4893), NSD1 (Entrez Gene ID: 64324), NTRK1 (Entrez Gene ID: 4914), NTRK3 (Entrez Gene ID: 4916), NUMA1 (Entrez Gene ID: 4926), NUP214 (Entrez Gene ID: 8021), NUP98 (Entrez Gene ID: 4928), OLIG2 (Entrez Gene ID: 10215), OMD (Entrez Gene ID: 4958), PAFAHIB2 (Entrez Gene ID: 5049), PALB2 (Entrez Gene ID: 79728), PAX3 (Entrez Gene ID: 5077), PAX5 (Entrez Gene ID: 5079), PAX7 (Entrez Gene ID: 5081), PAX8 (Entrez Gene ID: 7849), PBRM1 (Entrez Gene ID: 55193), PBX1 (Entrez Gene ID: 5087), PCM1 (Entrez Gene ID: 5108), PCSK7 (Entrez Gene ID: 9159), PDE4DIP (Entrez Gene ID: 9659), PDGFB (Entrez Gene ID: 5155), PDGFRA (Entrez Gene ID: 5156), PDGFRB (Entrez Gene ID: 5159), PER1 (Entrez Gene ID: 5187), PHOX2B (Entrez Gene ID: 8929), PICALM (Entrez Gene ID: 8301), PIK3CA (Entrez Gene ID: 5290), PIK3R1 (Entrez Gene ID: 5295), PIM1 (Entrez Gene ID: 5292), PLAG1 (Entrez Gene ID: 5324), PML (Entrez Gene ID: 5371), PMS1 (Entrez Gene ID: 5378), PMS2 (Entrez Gene ID: 5395), PMX1 (Entrez Gene ID: 5396), PNUTL1 (Entrez Gene ID: 5413), POU2AFI (Entrez Gene ID: 5450), POU5F1 (Entrez Gene ID: 5460), PPARG (Entrez Gene ID: 5468), PPP2R1A (Entrez Gene ID: 5518), PRCC (Entrez Gene ID: 5546), PRDM1 (Entrez Gene ID: 639), PRDM16 (Entrez Gene ID: 63976), PRF1 (Entrez Gene ID: 5551), PRKARIA (Entrez Gene ID: 5573), PRO1073 (Entrez Gene ID: 57018), PSIP2 (Entrez Gene ID: 11168), PTCH (Entrez Gene ID: 5727), PTEN (Entrez Gene ID: 5728), PTPN11 (Entrez Gene ID: 5781), RAB5EP (Entrez Gene ID: 9135), RAD51L1 (Entrez Gene ID: 5890), RAF1 (Entrez Gene ID: 5894), RALGDS (Entrez Gene ID: 5900), RANBP17 (Entrez Gene ID: 64901), RAP1GDS1 (Entrez Gene ID: 5910), RARA (Entrez Gene ID: 5914), RB1 (Entrez Gene ID: 5925), RBM15 (Entrez Gene ID: 64783), RECQL4 (Entrez Gene ID: 9401), REL (Entrez Gene ID: 5966), RET (Entrez Gene ID: 5979), ROS1 (Entrez Gene ID: 6098), RPL22 (Entrez Gene ID: 6146), RPNI (Entrez Gene ID: 6184), RuNDC2A (Entrez Gene ID: 92017), RUNX1 (Entrez Gene ID: 861), RUNXBP2 (Entrez Gene ID: 7994), SBDS (Entrez Gene ID: 51119), SDH5 (Entrez Gene ID: 54949), SDHB (Entrez Gene ID: 6390), SDHC (Entrez Gene ID: 6391), SDHD (Entrez Gene ID: 6392), SEPT6 (Entrez Gene ID: 23157), SET (Entrez Gene ID: 6418), SETD2 (Entrez Gene ID: 29072), SF3B1 (Entrez Gene ID: 23451), SFPQ (Entrez Gene ID: 6421), SFRS3 (Entrez Gene ID: 6428), SH3GL1 (Entrez Gene ID: 6455), SIL (Entrez Gene ID: 6491), SLC45A3 (Entrez Gene ID: 85414), SMARCA4 (Entrez Gene ID: 6597), SMARCB1 (Entrez Gene ID: 6598), SMO (Entrez Gene ID: 6608), SOCS1 (Entrez Gene ID: 8651), SOX2 (Entrez Gene ID: 6657), SRGAP3 (Entrez Gene ID: 9901), SRSF2 (Entrez Gene ID: 6427), SS18L1 (Entrez Gene ID: 26039), SSH3BP1 (Entrez Gene ID: 10006), SSX1 (Entrez Gene ID: 6756), SSX2 (Entrez Gene ID: 6757), SSX4 (Entrez Gene ID: 6759), STK11 (Entrez Gene ID: 6794), STL (Entrez Gene ID: 7955), SUFU (Entrez Gene ID: 51684), SUZ12 (Entrez Gene ID: 23512), SYK (Entrez Gene ID: 6850), TAF15 (Entrez Gene ID: 8148), TAL1 (Entrez Gene ID: 6886), TAL2 (Entrez Gene ID: 6887), TCEA1 (Entrez Gene ID: 6917), TCF1 (Entrez Gene ID: 6927), TCF12 (Entrez Gene ID: 6938), TCF3 (Entrez Gene ID: 6929), TCF7L2 (Entrez Gene ID: 6934), TCL1A (Entrez Gene ID: 8115), TCL6 (Entrez Gene ID: 27004), TET2 (Entrez Gene ID: 54790), TERT (telomerase reverse transcriptase; Entrez Gene ID: 7015), TFE3 (Entrez Gene ID: 7030), TFEB (Entrez Gene ID: 7942), TFG (Entrez Gene ID: 10342), TFPT (Entrez Gene ID: 29844), TFRC (Entrez Gene ID: 7037), THRAP3 (Entrez Gene ID: 9967), TIF1 (Entrez Gene ID: 8805), TLX1 (Entrez Gene ID: 3195), TLX3 (Entrez Gene ID: 30012), TMPRSS2 (Entrez Gene ID: 7113), TNFAIP3 (Entrez Gene ID: 7128), TNFRSF14 (Entrez Gene ID: 8764), TNFRSF17 (Entrez Gene ID: 608), TNFRSF6 (Entrez Gene ID: 355), TOP1 (Entrez Gene ID: 7150), TP53 (tumor protein p53; Entrez Gene ID: 7157), TPM3 (Entrez Gene ID: 7170), TPM4 (Entrez Gene ID: 7171), TPR (Entrez Gene ID: 7175), TRA@ (Entrez Gene ID: 6955), TRB@(Entrez Gene ID: 6957), TRD@ (Entrez Gene ID: 6964), TRIM27 (Entrez Gene ID: 5987), TRIM33 (Entrez Gene ID: 51592), TRIP11 (Entrez Gene ID: 9321), TSC1 (Entrez Gene ID: 7248), TSC2 (Entrez Gene ID: 7249), TSHR (Entrez Gene ID: 7253), TTL (Entrez Gene ID: 150465), U2AF1 (Entrez Gene ID: 7307), USP6 (Entrez Gene ID: 9098), VHL (Entrez Gene ID: 7428), WAS (Entrez Gene ID: 7454), WHSC1 (Entrez Gene ID: 7468), WHSC1L1 (Entrez Gene ID: 54904), WIF1 (Entrez Gene ID: 11197), WRN (Entrez Gene ID: 7486), WT1 (Entrez Gene ID: 7490), WTX (Entrez Gene ID: 139285), XPA (Entrez Gene ID: 7507), XPC (Entrez Gene ID: 7508), XPO1 (Entrez Gene ID: 7514), YWHAE (Entrez Gene ID: 7531), ZNF145 (Entrez Gene ID: 7704), ZNF198 (Entrez Gene ID: 7750), ZNF278 (Entrez Gene ID: 23598), ZNF331 (Entrez Gene ID: 55422), ZNF384 (Entrez Gene ID: 171017), ZNF521 (Entrez Gene ID: 25925), ZNF9 (Entrez Gene ID: 7555), and ZRSR2 (Entrez Gene ID: 8233)

In the embodiment, considering that the terminal regions (e.g., first 60 bp and last 60 bp) of the reference sequences of the selected cancer hotspot genes would only be covered by a single probe and might result in lower capture efficiency as compared with the non-terminal regions which would be covered by 2 probes in case of a 2× tiling, the reference sequences of the cancer hotspot genes may be elongated beyond both ends of the sequences. For example, exon 3 of the CTNNB1 gene is 228 bp in length; elongation of 75 bp at two ends of the sequence results in a 378-bp-long reference sequence of CTNNB1 exon 3 (SEQ ID NO. 33). Other reference sequences of the cancer hotspot genes may also be designed in a similar fashion. In addition, if the elongated region(s) of an exon overlaps with an adjacent exon or the elongated regions thereof, the two elongated reference sequences may be integrated into a single reference sequence covering both exons and all elongated regions.

The possible number of the hotspot gene targeting probes for the cancer hotspot genes may be calculated according to the aforementioned Equation (1). For example, a total of 20,874 probes that range from 50 bp to 120 bp can be designed for the 378-bp-long reference sequence of CTNNB1 exon 3 (SEQ ID NO. 33). Likewise, a total of 41,819 probes ranging 50-120 bp may be designed for a 673-bp-long reference sequence of a TERT promoter (SEQ ID NO. 34). A total of 49,345 probes ranging 50-120 bp may be designed for a 779-bp-long reference sequence of TP53 exons 2/3/4 (SEQ ID NO. 35). A total of 31,524 probes ranging 50-120 bp may be designed for a 528-bp-long reference sequence of TP53 exons 5/6 (SEQ ID NO. 36). A total of 12,496 probes ranging 50-120 bp may be designed for a 260-bp-long reference sequence of TP53 exon 7 (SEQ ID NO. 37). A total of 26,199 probes ranging 50-120 bp may be designed for a 453-bp-long reference sequence of TP53 exons 8/9 (SEQ ID NO. 39). A total of 12,283 probes ranging 50-120 bp may be designed for a 257-bp-long reference sequence of TP53 exon 10 (SEQ ID NO. 40). A total of 10,508 probes ranging 50-120 bp may be designed for a 232-bp-long reference sequence of TP53 exon 11 (SEQ ID NO. 41).

According to an embodiment of the present invention, the probe combination further includes one or more sets of exogenous gene targeting probes for negative control and quantitation. When sequences of one of the sets of exogenous gene targeting probes are aligned, an overall sequence of the aligned set exogenous gene targeting probes matches a reference sequence of an exogenous gene. In the aligned set of exogenous gene targeting probes, each of the exogenous gene targeting probes overlap with the immediately adjacent exogenous gene targeting probes by a portion of the length of the exogenous gene targeting probe. The portion of sequence overlapping may be, but is not limited to, 50% (i.e., 2× tiling density) or 75% (i.e., 4× tiling density).

The reference sequence of the exogenous gene is retrievable from the NCBI gene database. The exogenous gene may originate from lambda phage, E. coli, yeast, φX174, or other common microorganism. The possible number of the exogenous gene targeting probes for the exogenous genes may be calculated according to the aforementioned Equation (1). For example, a total of 478,682 probes that range from 50 bp to 120 bp can be designed for the 48502-bp-long reference sequence of lambda phage genome (GenBank Accession No. NC_001416).

In the embodiment, an external source of nucleotide fragments (e.g., spike-in DNA) corresponding to the sequences of the exogenous gene targeting probes is required. In other words, since the human genome, regardless of its hepatitis B or HCC status, does not contain genomic regions similar to the sequences of the exogenous gene targeting probes, the exogenous gene targeting probes theoretically would not capture any nucleotide fragments from genomic (gDNA) or circulating tumor DNA (ctDNA) of human samples if no nucleotide fragments corresponding to the sequences of the exogenous gene targeting probes are added externally during the detection process. As all nucleotide fragments captured by the exogenous gene targeting probes are theoretically the externally added nucleotide fragments, quantity and quality of the externally added nucleotide fragments can be manipulated, thus providing a reliable mean for absolute quantitation.

In an exemplary embodiment, four 120-bp regions on the lambda phage genome (SEQ ID NOs 42-45) were chosen for designing the lambda targeting probes according to the following selection criteria: a) no homology with human or HBV genome; b) unique among the lambda phage genome; c) GC content within a predefined range; d) no long monomer sequence (e.g., AAAAA); and/or e) no significant secondary structure as predicted by primer3, netprimer, and other primer design algorithms. As exemplified in Table 1, the full HBV targeting probes, the partial HBV targeting probes, the hotspot gene targeting probes, and the exogenous gene targeting probes may be used in combination to capture target nucleotide fragments that contains HBV DNA with or without viral-host junctions.

TABLE 1

| Reference | Tiling | Copy | Amount | Length Covered | SEQ ID |
| --- | --- | --- | --- | --- | --- |
| HBV Genome | 2X | 2N | 108 | 3191 | 1, 2 |
| HBV DR Region | 2X | 2N | 32 | 960 | 9, 13 |
| CTNNB1 exon 3 | 2X | 1N | 6 | 378 | 33 |
| TERT promoter | 2X | 1N | 11 | 673 | 34 |
| TP53 exons 2-11 | 2X | 1N | 39 | 2492 | 35-38, 40-41 |
| Lambda | 1X | 1N | 4 | 480 | 43-46 |

In another exemplary embodiment as depicted in Table 2, additional lambda targeting probes may be designed to cover elongated regions downstream of one of the four 120-bp regions (SEQ ID NOs 46-49) at a 2× or 4× tiling density. Additional sets (or copies) of the lambda targeting probes may also be used to simulate the two copies (2N) of the HBV targeting probes (one for genotype B and the other for genotype C) and one copy (1N) of the hotspot gene targeting probes, therefore resulting in a combination of 2×/1N, 2×/2N, 4×/1N, and 4×/2N lambda targeting probes corresponding to the elongated regions on the lambda genome.

TABLE 2

| Reference | Tiling | Copy | Amount | Length Covered | SEQ ID |
| --- | --- | --- | --- | --- | --- |
| HBV Genome | 2X | 2N | 106 | 3191 | 1, 2 |
| HBV DR Region | 2X | 2N | 30 | 960 | 9, 13 |
| CTNNB1 exon 3 | 2X | 1N | 6 | 378 | 33 |
| TERT promoter | 2X | 1N | 11 | 673 | 34 |
| TP53 exons 2-11 | 2X | 1N | 38 | 2509 | 35-37, 39-41 |
| Lambda | 2X | 1N | 3 | 240 | 46 |
|  | 2X | 2N | 6 | 240 | 47 |
|  | 4X | 1N | 3 | 180 | 48 |
|  | 4X | 2N | 6 | 180 | 49 |
|  | 1X | 1N | 5 | 600 | 50-54 |
| GAPDH | 2X | 1N | 3 | 240 | 55 |
| GdX | 2X | 1N | 3 | 240 | 56 |

Further, GC content has been reported to affect sequencing coverage, exhibiting approximately 3 fold difference among samples with low GC ratio (GC=0.3, coverage=0.6×), optimal GC ratio (GC=0.48, coverage=1.3×), and high GC ratio (0.7, coverage=0.4×). Therefore, as depicted in Table 2, additional sets of lambda targeting probes may also be designed to internally control the GC content of the probes. Five 120-bp regions on the lambda phage genome (SEQ ID NOs 50-54) were chosen according to the following selection criteria: a) no homology with human or HBV genome; b) unique among the lambda phage genome; c) GC content within a predefined range; d) no long monomer sequence (e.g., AAAAA); and e) no significant secondary structure as predicted by primer3, netprimer, and other primer design algorithms. Consequently, five 120-bp-long regions having GC contents of 0.3, 0.4, 0.5, 0.6, and 0.68 are selected for designing the five additional sets of lambda targeting probes (1×/1N).

According to an embodiment of the present invention, the probe combination further includes one or more sets of endogenous gene targeting probes for positive internal control and relative quantitation. When sequences of one of the sets of endogenous gene targeting probes are aligned, an overall sequence of the aligned set of endogenous gene targeting probes matches a reference sequence of an endogenous gene. In the aligned set of endogenous gene targeting probes, each of the endogenous gene targeting probes overlap with the immediately adjacent endogenous gene targeting probes by a portion of the length of the endogenous gene targeting probe. The portion of sequence overlapping may be, but is not limited to, 50% (i.e., 2× tiling density) or 75% (i.e., 4× tiling density).

The reference sequence of the endogenous gene is retrievable from the NCBI gene database. In the embodiment, the endogenous gene is intrinsic of the human genome and may include, but is not limited to, at least one of the following genes, as identified by Entrez Gene IDs according to the NCBI gene database (www.ncbi.nlm.nih.gov/entrez/query.fcgi?db=gene): GAPDH (glyceraldehyde-3-phosphate dehydrogenase; Entrez Gene ID: 2597), UBL4A (ubiquitin like 4A; GdX; Entrez Gene ID: 8266), HPRT1 (Entrez Gene ID: 3251), TBP (Entrez Gene ID: 6908), B2M (Entrez Gene ID: 567), RPL13A (Entrez Gene ID: 23521), RN18S1 (Entrez Gene ID: 100008588), C1orf43 (Entrez Gene ID: 25912), CHMP2A (Entrez Gene ID: 27243), EMC7 (Entrez Gene ID: 56851), GPI (Entrez Gene ID: 2821), PSMB2 (Entrez Gene ID: 5690), PSMB4 (Entrez Gene ID: 5692), RAB7A (Entrez Gene ID: 7879), REEP5 (Entrez Gene ID: 7905), SNRPD3 (Entrez Gene ID: 6634), VCP (Entrez Gene ID: 7415), VPS29 (Entrez Gene ID: 51699), ACTB (Entrez Gene ID: 60), PPIA (Entrez Gene ID: 5478), GUSB (Entrez Gene ID: 2990), HSP90AB1 (Entrez Gene ID: 3326), RPLP0 (Entrez Gene ID: 6175), TFRC (Entrez Gene ID: 7037), UBC (Entrez Gene ID: 7316).

The possible number of the endogenous gene targeting probes for the endogenous genes may be calculated according to the aforementioned Equation (1). For example, a total of 113,458 probes that range from 50 bp to 120 bp can be designed for the 1682-bp-long reference sequence of GAPDH gene. Likewise, a total of 248,429 probes that range from 50 bp to 120 bp can be designed for the 3583-bp-long reference sequence of GdX gene.

In the embodiment, the endogenous genes are chosen to enhance reliability of sequence detection; that is, the endogenous genes are adopted for being common housekeeping genes that are stably expressed and have not been found to variate in tumors. It can understood that quantification according to detection of only the cancer hotspot genes could be unreliable as structural variation of the cancer hotspot genes, such as CTNNB1, TP53, TERT, and other cancer related genes listed above, have been reported in tumor samples and that their copy numbers may change during tumorigenesis due to deletion, duplication, or other structural variations. Therefore, in an exemplary embodiment as depicted in Table 2, probes targeting a 240-bp region on the GAPDH gene (SEQ ID NO. 55) at a 2× tiling density and probes targeting a 240-region of the GdX gene (SEQ ID NO. 56) at a 2× tiling are included in the probe combination as internal control. The 240-bp regions on the GAPDH and GdX genes do not have homology to HBV genome, long monomers, significant secondary structure, or GC content out of a predefined range. Additional advantage of adopting the GdX gene is that GdX can also be used to identify gender of the test subject.

In some embodiments of the present invention, the probes are each labeled with a marker molecule to facilitate detection and quantitation. The marker molecule may include, but are not limited to, biotin, fluorescent protein, luminescent protein, antibody, radioactive compounds, or any combination thereof.

Another aspect of the present invention provides a method for detecting infection with DNA virus (e.g., HBV, HPV, EBV, HHV-8, HTLV, MCV, or other DNA viruses) or viral infection associated cancer (e.g., hepatocellular carcinoma, cervical cancer, nasopharyngeal cancer, lymphoma, Merkel cell carcinoma, or other cancers associated with infection with the DNA viruses). In an embodiment, the method includes the steps of: extracting nucleic acids from a specimen of a subject; amplifying the nucleic acids; hybridizing the nucleic acids with the probe combination according to the various embodiments mentioned above to capture target nucleotide fragments; sequencing the target nucleotide fragments; and analyzing the target nucleotide fragments.

In the embodiment, the nucleic acids may include viral nucleic acids, host genome nucleic acids, and nucleic acids with viral-host junction, and may be DNA, RNA, or polynucleotides. Extraction of the nucleic acids may be performed by precipitation, chromatography and/or magnetic bead capturing. The specimen from which the nucleic acids are extracted may be biological fluid (e.g., blood, sweat, saliva, tears, urine, lymph, or interstitial fluid) or tissues (e.g., liver tissue). Amplification of the extracted nucleic acids may be performed by DNA cloning, polymerase chain reaction (PCR), reverse transcription PCR (RT-PCR), nested-PCR, quantitative (qPCR) and/or digital PCR. The target nucleotide fragments may be captured by the probe combination via hybridization (e.g., southern blot hybridization, in situ hybridization, or northern blot hybridization) and/or lockdown (e.g., bead-based method or chip-based method). The captured target nucleic acids may be sequenced by NGS (e.g., massively parallel sequencing, single molecule sequencing, or NanoString). Maxam-Gilbert sequencing, Sanger sequencing, pyrosequencing, and/or DNA microarray.

In an alternative embodiment, the amplification step and the hybridization step may be reversed. In other words, the method according to another embodiment of the present invention includes the steps of: extracting nucleic acids from a specimen of a subject; hybridizing the nucleic acids with the probe combination according to the various embodiments of the present invention to capture target nucleotide fragments; amplifying the captured target nucleotide fragments; sequencing the target nucleotide fragments; and analyzing the target nucleotide fragments.

Analysis and quantitation of the target nucleic acids captured by the probe combination may be performed as follows. Raw reads (RR) are generated directly from the NGS sequencing instrument. Low quality reads among the raw reads are excluded to obtain high quality reads (HQR). The HQRs are compressed into unique reads (UR); in other words, HQRs having completely identical sequences are collapsed into a single unique read, while the information regarding the copy numbers (redundancy) thereof is retained. Finally, URs with low redundancies are excluded to result in high redundancy unique reads (HRLTR). Further, the total number of reads included in the high redundancy unique reads (RiHRUR) can be calculated by the retained redundancy information during the compression process.

In an embodiment, the bioinformatics analytic methodology adopted in analyzing the NGS data set is summarized in Table 3.

TABLE 3

| Analysis | Preferred Embodiment | Prior Art |
|---|---|---|
| Junction Detection | Direct identification of HBV-human junction | Direct identification of HBV-human junction |
| Mapping Method | BLAST | SOAP2 (for initial mapping) BWA (for junction detection) |
| Pair-end Reads | Viewed as individual reads | Merge whenever possible (overlap >5 bp and mismatch rate <0.2 |
| Low Quality Read | A read whose bases with quality value ≤5 occupying 50% of the read length | A read whose bases with quality value ≤5 occupying 50% of the read length |
| Redundancy | Reads with redundancy <5 excluded | Duplicated reads removed |
| Mapping Criteria | BLAST e-value <$1^{-10}$ for both HBV and human (~20-40 bp) | 30 bp for both HBV and human |
| Quantification | Total number of reads | Total number of unique reads; Normalized total number of paired-reads; Merge neighboring junctions (20 bp) |

Table 3 also compares the methodology of the embodiment with that reported by Zhao. As shown in Table 3, some major differences between the two include: Zhao merges junctions of close vicinity, whereas the methodology of the present embodiment merges junctions based on sequence similarity. Also, Zhao removes duplicated reads, considering only unique junctions, whereas the methodology of the present embodiment excludes reads having redundancies of less than 5, retains redundancy information, and quantifies junctions based on the total number of reads for single unique junction.

Validation of Probe Specificity

Probes targeting TP53 exons 2-11 (SEQ ID NOs 35-38, 40-41) designed according to an embodiment of the present invention were hybridized with HCC tumor genomic DNA (gDNA), non-tumor gDNA, and ctDNA of an HCC patient and quantified by qPCR. MicroRNA miR-122 that is conserved among vertebrates and highly expressed in the liver was also quantified as a negative control.

TABLE 4

Post-Hybridization Retention Ratio

| Sample Type | TP53 | miR-122 | Fold Difference |
|---|---|---|---|
| HCC Tumor gDNA | 3.40% | 0.01% | 274.37 |
| Non-Tumor gDNA | 4.61% | 0.02% | 268.72 |
| ctDNA | 2.65% | 0.26% | 10.26 |

As demonstrated in Table 4, the significantly higher post-hybridization retentions of TP53 over miR-122 in all of the three sample types indicated that TP53 fragments were successfully hybridized, captured, and recovered by the TP53 targeting probes; in contrast, miR-122 fragments were washed off during the procedure as the TP53 targeting probes have no specificity to miR-122. Table 4 also shows that the amounts of TP53 fragments captured by the TP53 targeting probes from the genomic DNA were over 250 folds higher than that of miR-122 fragments, and that TP53 fragments captured from ctDNA were over 10 times more concentrated than that miR-122 fragments. The results demonstrated that the TP53 targeting probes is sequence specific and can selectively capture TP53 gene fragments from DNA samples.

Meanwhile, as shown in Table 5, a total of 26 HCC tumor gDNA samples are enriched by the probe combination listed above in Table 1 and sequenced by next generation sequencing (NGS) for analysis of presence of HBV genome, HBV-human junction (denoted "Junction") and cancer hotspot genes (including CTNNB1, TERT, and TP53). The HBV-human junction is indicative of HBV integration into human genome. The host genome ratio in Table 5 is the calculated length ratios of the captured sequences over the human genome. As demonstrated in Table 5, the significant differences between the calculated host genome ratios and the observed NGS read ratios indicated successful enrichment of the HBV genome, cancer hotspot genes and HBV-human junction by the probe combination.

TABLE 5

| | NGS Dataset Read Ratio | Host Genome Ratio |
|---|---|---|
| HBV | 35.01% | <0.0001% (32.15 kb) |
| Junction | 0.72% | <0.0001% (3.00 kb) |
| CTNNB1/TERT/TP53 | 33.57% | <0.0001% (3.56 kb) |

It is to be understood that the estimated 3 kb junction length in the host genome was calculated by estimating that a single junction would have a detection range of 150 bp. Therefore, a single integration event, which results in two junctions, would be represented by 300 bp of junction regions. By using a rough estimate of 10 detectable junctions per patient, the estimated junction length of an individual patient was hence set at 3 kb (i.e., 300 bp×10). The length of integrated HBV (excluding free-form non-integrated HBV) was then estimated at 32.15 kb (i.e., 3.215 kb×10). The estimation of the junction and HBV ratio in the human genome presented herein is very crude and most likely an over-estimate, which would result in an under-estimation of the enrichment efficiency of junctions and HBV.

Figure 3:
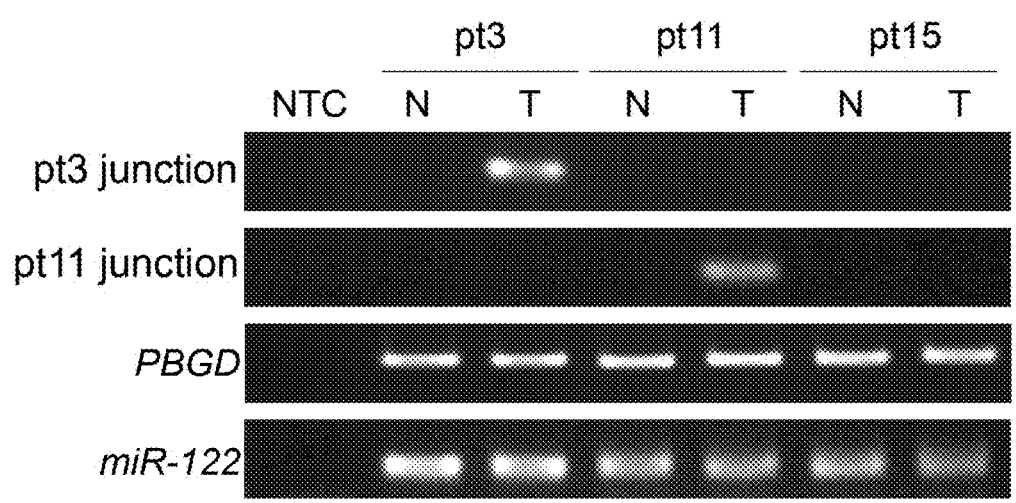
FIG. 3 is an experimental result showing the selective hybridization of the probes designed in accordance with an embodiment of the present invention.

Referring now to FIG. 3. Junction targeting probes designed according to the embodiments of the present invention are demonstrated to selectively capture DNA fragments having specific viral-host junctions. HCC tumor gDNA samples were collected from tumor (denoted T) and non-tumor (denoted N) tissues of three HCC patients (denoted pt3, pt 11 and pt15), and were hybridized with probe 1 (denoted pt3 junction) and probe 2 (denoted pt 11 junction) that were designed according to sequences of HBV-human junctions in pt3 and pt 11, respectively. Western blot analysis shown in FIG. 3 indicated that probe 1 selectively hybridized with tumor gDNA of patient pt3 and probe 2 selectively hybridized with tumor gDNA of patient pt 11. NTC refers to "no template control" and was used a negative control for the experiment; whereas PBGD (i.e., porphobilinogen deaminase gene) and miR-122 were used as positive controls.

Figure 4A:
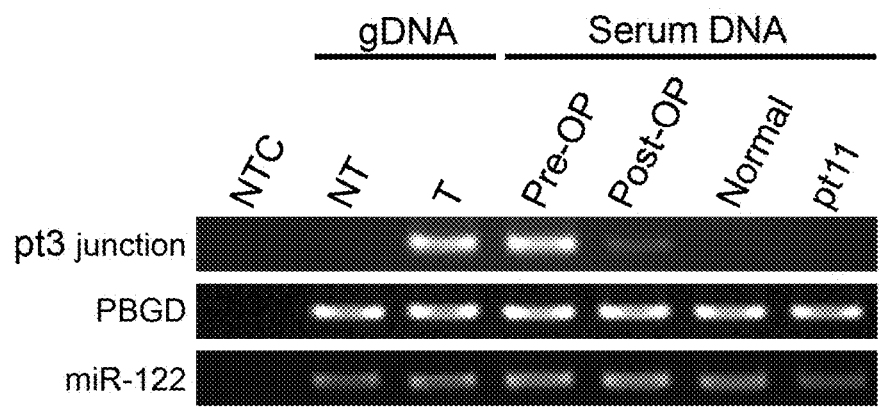
FIGS. 4A and 4B are experimental results showing the specificity of the probes designed in accordance with an embodiment of the present invention.
Figure 4B:
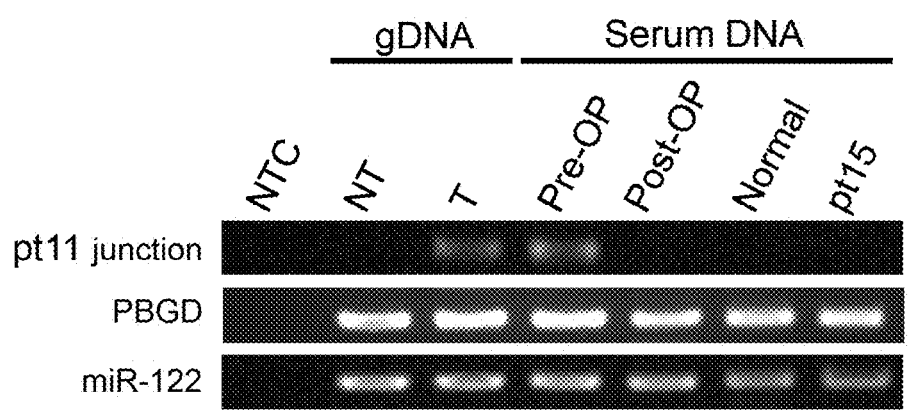

Referring now to FIGS. 4A and 4B. Probe 1 (denoted pt3 junction) was then used to detect presence of HBV-human junction in genomic DNA and serum DNA of patient pt3. As shown in FIG. 4A, a pt3 specific HBV-human junction was observed in tumor gDNA and pre-operation (pre-OP) and post-operation (post-OP) serum DNA of patient pt3. Such junction was not observed in patient pt 11 or in non-HCC HBV positive patient (denoted "Normal"). Similarly, as shown in FIG. 4B, when probe 2 (denoted pt 11 junction) was used to detect presence of HBV-human junction in genomic DNA and serum DNA of patient pt 11, a pt 11 specific HBV-human junction was observed in tumor gDNA and pre-operation (pre-OP) serum DNA of patient pt11. Such junction was not observed in patient pt 15 or in non-HCC HBV positive patient (denoted "Normal").

Validation of Capture Efficiency

The probe combination listed above in Table 2 was used to analyze DNA fragments in a pair of tumor gDNA and plasma ctDNA samples (i.e., DNA samples from a single HCC patient) for determining the capture efficiency of the probe combination in different sample types. As shown in the NGS statistics in Table 6, tumor gDNA was 10-18 times higher in full HBV, partial HBV, and HBV-human junction reads than plasma ctDNA, demonstrating a higher capture efficiency of the probe combination in tumor gDNA samples. In addition, 8 of the 10 junction types identified in the tumor gDNA sample were with significant read numbers (>947), indicating a junction recovery rate of 75%.

TABLE 6

| | Sample Type | |
|---|---|---|
| | Tumor gDNA | Plasma ctDNA |
| Raw Reads (RR) | 3,933,540 | 2,674,212 |
| High Quality Reads (HQR) | 3,919958 | 2,658,014 |

TABLE 6-continued

| | Sample Type | |
|---|---|---|
| | Tumor gDNA | Plasma ctDNA |
| Unique Reads (UR) | 1,271,268 | 2,400,413 |
| High Redundancy Unique Reads (HRUR) | 23,245 | 3,809 |
| Reads included in HRUR (RiHRUR) | 2,341,219 | 140,452 |
| Partial HBV | 72,346 | 7,514 |
| Full HBV | 355,838 | 20,130 |
| Unique Junction Reads | 512 | 32 |
| Total Junction Reads | 16,242 | 1,184 |
| Junction Type | 10 | 28 |
| CTNNB1 exon 3 | 46,177 | 6,779 |
| TERT | 19,851 | 17,355 |
| TP53 exon 2/3/4 | 43,050 | 17,272 |
| TP53 exon 5/6 | 42,423 | 11,495 |
| TP53 exon 7 | 14,701 | 3,903 |
| TP53 exon 8/9 | 26,181 | 5,447 |
| TP53 exon 10 | 13,403 | 6,111 |
| TP53 exon 11 | 8,772 | 1,980 |
| TP53 total | 148,530 | 46,208 |

Figure 5A:
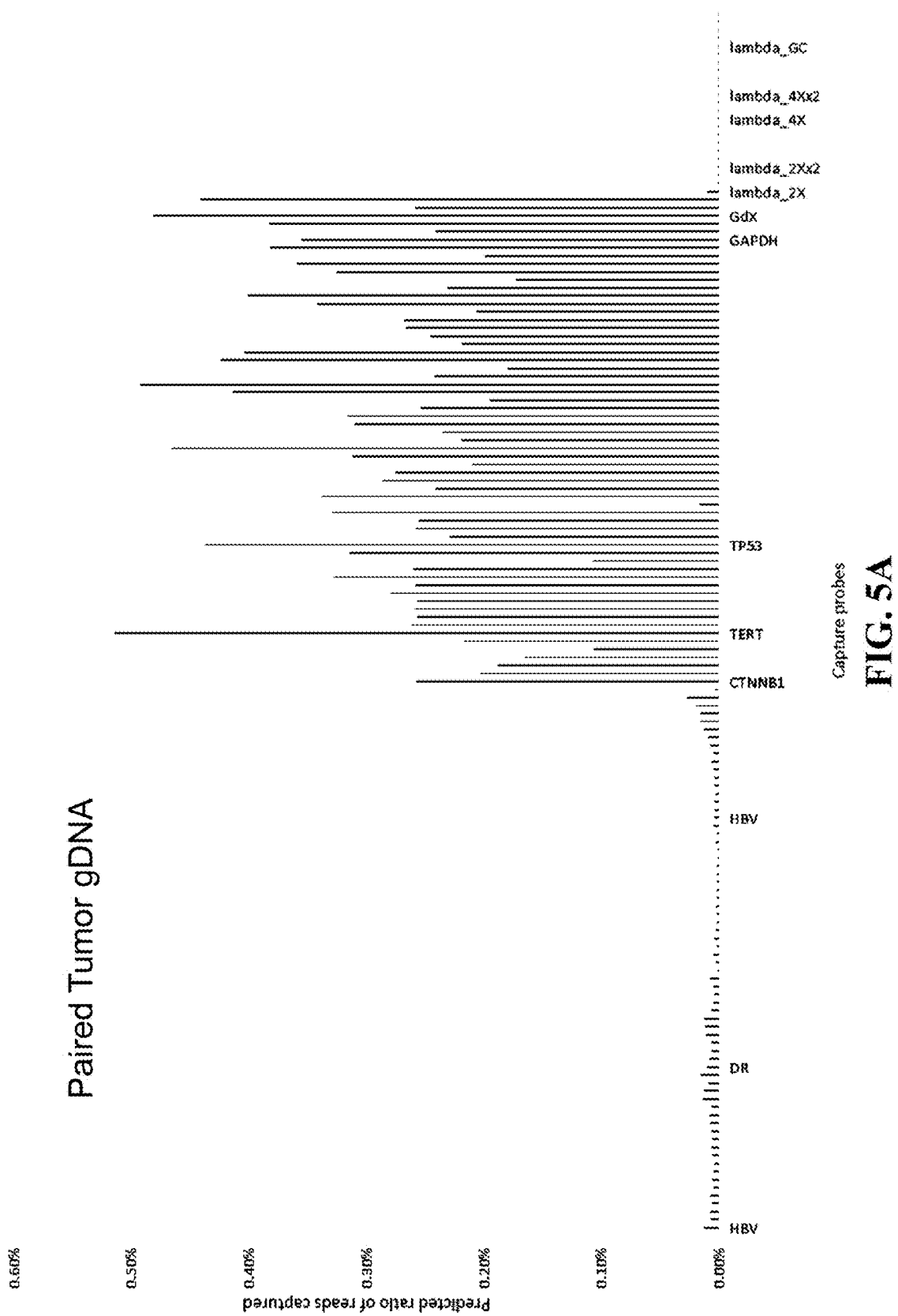
FIG. 5A is a heat map converted bar chart showing the next generation sequencing (NGS) results at various genetic regions in a paired tumor genomic DNA (gDNA) sample by using a probe combination in accordance with an embodiment of the present invention.
Figure 5B:
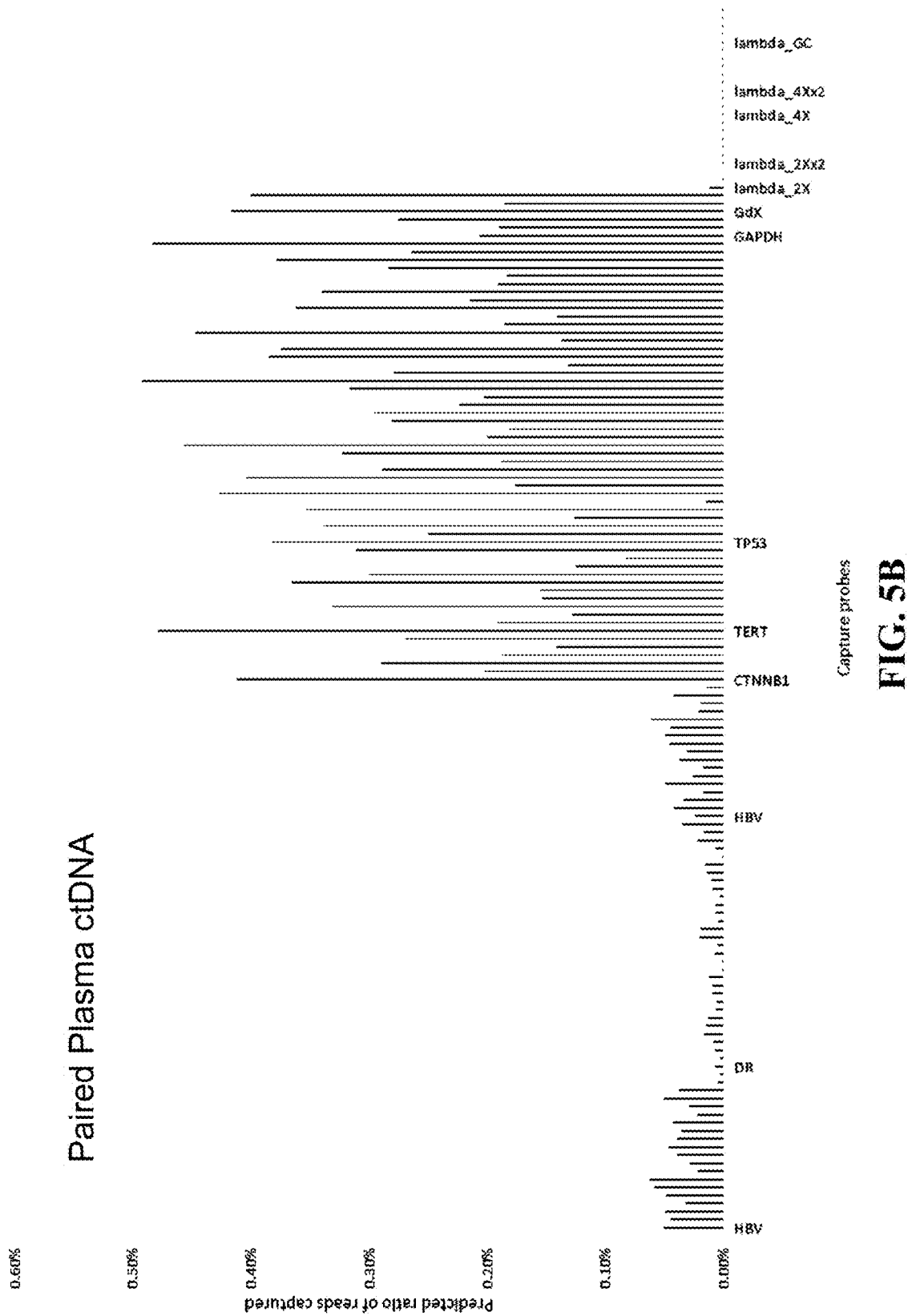
FIG. 5B is a heat map converted bar charts showing the NGS results at various genetic regions in a paired plasma circulating tumor DNA (ctDNA) sample by using the probe combination in accordance with an embodiment of the present invention.
Figure 6:
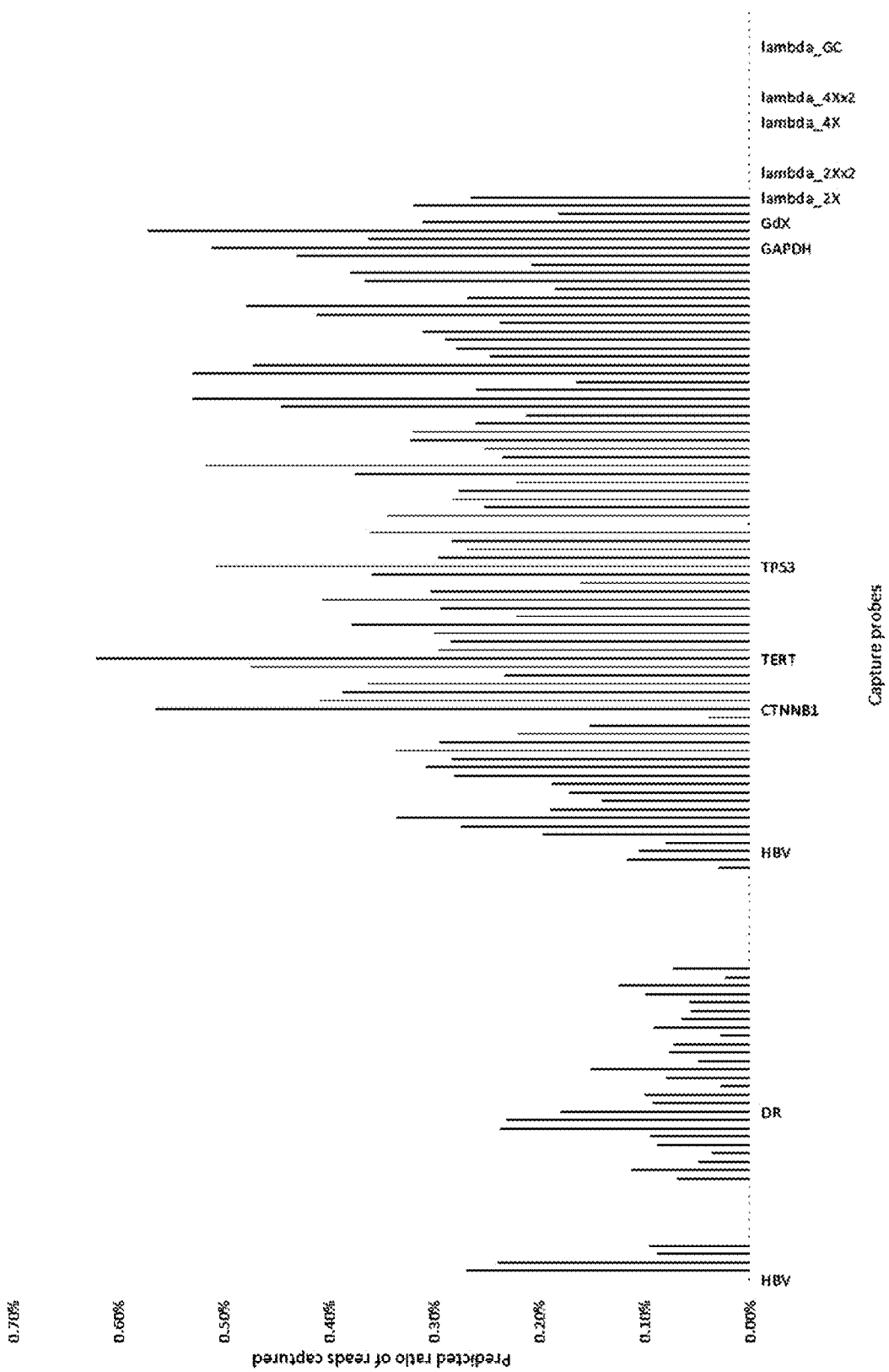
FIG. 6 is a heat map converted bar charts showing the NGS results at various genetic regions in a tumor gDNA sample by using a probe combination in accordance with an embodiment of the present invention.

FIG. 5A and FIG. 5B are heat map converted bar charts showing the predicted ratio of sequenced NGS reads captured by each of the probes. Meanwhile, FIG. 6 shows the NGS results of tumor gDNA sample of another HCC patient using the same probe combination (as in Table 2).

Referring now to FIG. 7. In addition to detection of HBV DNA and HBV integration into human genome, the probe combination according to the embodiments of the present invention can also detect cancer associated gene mutations. As shown in FIG. 8, NGS analysis of DNA samples from male and female HCC patients with genotype B HBV infection revealed different numbers of unique HBV-human junctions detected (denoted "Junction Type"), unique junctions detected in the TERT or MLL4 region (denoted "TERT/MLL4 integration"), and known cancer hotspot mutations in the TERT promoter or CTNNB1 exon 3 region (denoted "TERT/CTNNB1 mutations") among the patients.

Benefits and Advantages

The probe combination and analytic methodology according to the embodiments of the present invention exhibits significantly superior sensitivity and efficiency over the prior art. As compared with the results reported by Li as shown in Table 7, the target nucleotide fragments captured by the probe combination of a preferred embodiment of the present invention (as in Table 1) has significantly higher HBV ratio, higher junction reads, and lower human ratio.

TABLE 7

| Probes | Preferred Embodiment 70% HBV targeting 28% human targeting | Prior Art 100% HBV targeting |
|---|---|---|
| HBV-only Reads | 37.68% | 0.08% |
| Partial HBV Reads | 5.61% | n/a |
| Junction Reads | 0.78% | 0.01% |
| Human Reads | 29.75% | 83.70% |

In addition, analysis of the NGS data set reported by Zhao using the bioinformatics analytic methodology for identifying viral-host junctions according to the embodiments of the present invention also showed that 97.5% of the reads of Zhao were human, with only 1.49% HBV, 1.43% partial HBV and 1% junction, reconfirming the poor efficiency of existing HBV capture probes in enrichment of HBV fragments and HBV-human junctions. Furthermore, while Zhao only reported to identify 157 junctions, analysis of Zhao's NGS data set by the analytic methodology of the embodiments of the present invention reveal 469 junctions and recover nearly 80% of Zhao's junctions. These results demonstrate that the analytic methodology of the embodiments of the present invention are highly sensitive in detection of viral integration and can identify significantly more viral-host junctions than the existing art.

Further, as compared with the direct sequencing approaches of Jiang and Sung, the probe combination and analytic methodology according to the embodiments of the present invention generate only about 5 million 150-bp reads in a typical NGS data set (i.e., 80% less in read number or 60% less in total nucleotides than Jiang); yet, as many as 307,101 HBV reads and 69,198 junction reads can be identified from the 5 million reads. The results also demonstrate that the embodiments of the present invention are not only sensitive but also highly efficient in identification of viral integration.

In sum, the present invention according to the aforementioned embodiments provides a powerful and versatile tool for detection of viral infection and viral infection induced cancer. The embodiments of the present invention can be applied to detect presence of various types of DNA viruses and viral integration. The probe combination designed according to the embodiments ensures optimal viral/host sequence coverage and considers genetic stability, and is thus demonstrated to be highly sensitive, efficient, and reliable.

Previous descriptions are only embodiments of the present disclosure and are not intended to limit the scope of the present disclosure. Many variations and modifications according to the claims and specification of the disclosure are still within the scope of the claimed disclosure. In addition, each of the embodiments and claims does not have to achieve all the advantages or characteristics disclosed. Moreover, the abstract and the title only serve to facilitate searching patent documents and are not intended in any way to limit the scope of the claimed disclosure.

What is claimed is:

1. A probe combination, comprising:
   a first group of probes, each including a marker that comprises at least one of biotin, fluorescent protein, luminescent protein, antibody and radioactive compounds,
   wherein each of the first group of probes corresponds to a reference sequence, the reference sequence being a sub-segment of a human genome that includes a consensus sequence of hepatitis B virus (HBV) genotype B and C,
   wherein the first group of probes has partially overlapping first tiling density,
   wherein each of the first group of probes has a same length,
   wherein the first group of probes collectively corresponds to a full length of the reference sequence;
   wherein the length of each of the first group of probes ranges from 50 bp to 120 bp; and
   a second group of probes, each including a marker comprising at least one of biotin, fluorescent protein, luminescent protein, antibody and radioactive compounds,
   wherein each of the second group of probes corresponds to a sub-segment of a direct repeat (DR) region in the reference sequence, the DR region being a subset of the reference sequence;
   wherein the DR region of the reference sequence comprises at least one of SEQ ID NO: 6-9 and 10-13,
   wherein the second group of probes has partially overlapping second tiling density,
   wherein each of the second group of probes has a same length,
   wherein an overall distribution of the second group of probes matches a full length of the DR region;
   wherein the first group of probes starts at a different position than the second group of probes; and
   wherein the first group of probes and the second group of probes are not fully aligned.

2. The probe combination according to claim 1, wherein the HBV genotype comprises genotype A, genotype D, genotype E, genotype F, genotype Q, genotype H, genotype I and genotype J.

3. The probe combination according to claim 1, further comprising:
   one or more sets of hotspot gene targeting probes,
   wherein when sequences of each of the one or more sets of hotspot gene targeting probes are aligned, an overall sequence of the aligned sequences of each of the one or more sets of hotspot gene targeting probes matches a cancer hotspot gene of the reference sequence, and
   hotspot gene targeting probes, each of the hotspot gene targeting probes overlaps with one or two adjacent hotspot gene targeting probes by a portion of a length of the corresponding hotspot gene targeting probe.

4. The probe combination according to claim 3, wherein the cancer hotspot gene comprises at least one of CTNNB1 gene, TERT gene, and TP53 gene.

5. The probe combination according to claim 3, wherein the cancer hotspot gene of the reference sequence comprises at least one of SEQ ID NOs. 33-41.

6. The probe combination according to claim 1, further comprising:
   one or more sets of exogenous gene targeting probes,
   wherein when sequences of each of the one or more sets of exogenous gene targeting probes are aligned, an overall sequence of the aligned sequences of each of the one or more sets of exogenous gene targeting probes matches an exogenous gene of the reference sequence, and
   in the aligned sequences of each of the one or more sets of exogenous gene targeting probes, each of the exogenous gene targeting probes overlaps with one or two adjacent exogenous gene targeting probes by a portion of a length of the exogenous gene targeting probe.

7. The probe combination according to claim 6, wherein the exogenous gene originates from a lambda phage.

8. The probe combination according to claim 6, wherein the exogenous gene of the reference sequence comprises at least one of SEQ ID NOs. 42-54.

9. The probe combination according to claim 6, further comprising:
one or more sets of endogenous gene targeting probes,
wherein when sequences of each of the one or more sets of endogenous gene targeting probes are aligned, an overall sequence of the aligned sequences of each of one or more sets of endogenous gene targeting probes matches an endogenous gene of the reference sequence, and
in the aligned sequences of each of the one or more sets of endogenous gene targeting probes, each of the endogenous gene targeting probes overlaps with one or two adjacent endogenous gene targeting probes by a portion of a length of the endogenous gene targeting probe.

10. The probe combination according to claim 9, wherein the endogenous gene comprises at least one of GAPDH gene and GdX gene.

11. The probe combination according to claim 9, wherein the endogenous gene of the reference sequence comprises at least one of SEQ ID NO. 55 and SEQ ID NO. 56.

12. The probe combination according to claim 1, wherein the probe combination is used for capturing target nucleotide fragments having viral-host junctions from deoxyribonucleic acid (DNA) obtained for a specimen of a subject infected with HBV.

13. The probe combination according to claim 12, wherein the DNA comprises genomic DNA and circulating tumor DNA of the subject.

14. The probe combination according to claim 12, wherein the specimen comprises biological fluid and liver tissues.

15. The probe combination according to claim 1, wherein the full length of the reference sequence comprises at least one of SEQ ID NOs.1 and 2.

16. The probe combination according to claim 1, wherein the first tiling density equals the second tiling density.

17. The probe combination according to claim 16, wherein the first tiling density is 2×.

18. The probe combination according to claim 16, wherein the first tiling density is 4×.

19. The probe combination according to claim 1, wherein a copy number of each of the first group of probes and a copy number of each of the second group of probes are identical.

20. The probe combination according to claim 19, wherein a copy number of each of the first group of probes is 1.

21. The probe combination according to claim 1, wherein a copy number of each of the first group of probes is 1 or 2.

22. The probe combination according to claim 1, wherein the length of each of the second group of probes is identical to the length of the first group of probes.

23. A probe combination, comprising:
a plurality of probes having partially overlapping tiling density, each of the plurality of probes provided with a marker that comprises at least one of biotin, fluorescent protein, luminescent protein, antibody and radioactive compounds,
wherein each of the plurality of probes has a same length,
wherein the length of plurality of probes ranges from 50 bp to 120 bp,
wherein each of the plurality of probes corresponds to a sub-segment of a reference sequence, the reference sequence being a sub-segment of a human genome that includes a consensus sequence of hepatitis B virus (HBV) genotype B and C,
wherein the reference sequence comprises a direct repeat (DR) region therein, the DR region being a subset of the reference sequence,
wherein the DR region of the reference sequence comprises at least one of SEQ ID NO: 6-9 and 10-13,
wherein the plurality of probes collectively corresponds to a full length of the reference sequence,
wherein a number density of the plurality of probes that corresponds to the DR region is greater than a number density of the plurality of probes that corresponds to regions outside the DR region of the reference sequence.

24. The probe combination according to claim 23, wherein the full length of the reference sequence comprises at least one of SEQ ID NOs. 1 and 2.

25. The probe combination according to claim 23,
wherein a tiling distribution of the plurality of probes has a tiling density;
wherein the tiling density is 2×.

26. The probe combination according to claim 23,
wherein a tiling distribution of the probes has a tiling density;
wherein the tiling density is 4×.

27. The probe combination of claim 23, wherein a copy number of each of the plurality of probes is 1.

28. The probe combination of claim 23, wherein a copy number of each of the plurality of probes is 2.

* * * * *